US012799514B2

(12) United States Patent
Tanaka et al.

(10) Patent No.: US 12,799,514 B2
(45) Date of Patent: Nov. 17, 2026

(54) β-FRUCTOFURANOSIDASE

(71) Applicants: KYOTO PREFECTURAL PUBLIC UNIVERSITY CORPORATION, Kyoto (JP); MEIJI CO., LTD., Tokyo (JP)

(72) Inventors: Shun-ichi Tanaka, Kyoto (JP); Mamiko Yano, Kyoto (JP); Keiichi Ueno, Tokyo (JP); Takumi Miyatake, Tokyo (JP); Satoshi Takasugi, Tokyo (JP)

(73) Assignees: KYOTO PREFECTURAL PUBLIC UNIVERSITY CORPORATION, Kyoto (JP); MEIJI CO., LTD., Tokyo (JP)

( * ) Notice: Subject to any disclaimer, the term of this patent is extended or adjusted under 35 U.S.C. 154(b) by 284 days.

(21) Appl. No.: 18/692,604

(22) PCT Filed: Oct. 4, 2022

(86) PCT No.: PCT/JP2022/037083

§ 371 (c)(1),
(2) Date: Mar. 15, 2024

(87) PCT Pub. No.: WO2023/058637

PCT Pub. Date: Apr. 13, 2023

(65) Prior Publication Data

US 2024/0384317 A1 Nov. 21, 2024

(30) Foreign Application Priority Data

Oct. 4, 2021 (JP) ................................ 2021-163489

(51) Int. Cl.
*C12P 19/04* (2006.01)
*C12N 9/26* (2006.01)
*C12P 19/14* (2006.01)

(52) U.S. Cl.
CPC ............ *C12P 19/04* (2013.01); *C12N 9/2431* (2013.01); *C12P 19/14* (2013.01); *C12Y 302/01026* (2013.01)

(58) Field of Classification Search
CPC ...................... C12N 9/2431; C12Y 302/01026
See application file for complete search history.

(56) References Cited

U.S. PATENT DOCUMENTS 7,655,449 B2 * 2/2010 Nakamura ..... C12Y 302/01026 435/320.1
2008/0187970 A1 8/2008 Nakamura et al.
2016/0319263 A1 11/2016 Tochio et al.
2018/0044651 A1 2/2018 Tochio et al.

FOREIGN PATENT DOCUMENTS

JP 2010-273580 12/2010
JP WO2015/099166 3/2017
JP WO2016/143873 12/2017
WO 2005/085447 9/2005
WO 2015/099166 7/2015

OTHER PUBLICATIONS

International Preliminary Report on Patentability issued Apr. 9, 2024 in International Application No. PCT/JP2022/037083, 12 pages.
Extended European Search Report issued Oct. 17, 2025 in European Patent Application No. 22878505.1, pp. 1-16.
Sucrose Alpha-Glucosidase Activity: "Glycoside hydrolase family 32 protein—Athelia psychrophile", Jul. 6, 2016, pp. 1-5.
"UNIPROT:A0A1W5VKD7", Jul. 5, 2017, p. 1.
Susu Han et al., "Improved production of fructooligosaccharides (FOS) using a mutant strain of *Aspergillus oryzae* S719 overexpressing β-fructofuranosidase (FTase) genes", LWT—Food Science and Technology, vol. 146, 111346, pp. 1-11 (Jul. 1, 2021).
International Search Report issued Dec. 20, 2022 in International (PCT) Application No. PCT/JP2022/037083.
Gibson, Glenn R. et al., "Dietary Modulation of the Human Colonic Microbiota: Introducing the Concept of Prebiotics", J Nutr. 1995, vol. 125, No. 6, pp. 1401-1412.
Tochio, Takumi et al., "1-Kestose, the Smallest Fructooligosaccharide Component, Which Efficiently Stimulates Faecalibacterium prausnitzii as Well as Bifidobacteria in Humans", Foods, 2018, vol. 7, No. 140, 11 pages.
Hidaka, Hidemasa et al., "A Fructooligosaccharide-producing Enzyme from Aspergillus niger ATCC 20611", Agric. Biol. Chem., 1988, vol. 52, No. 5, pp. 1181-1187.

(Continued)

*Primary Examiner* — David H Kruse
(74) *Attorney, Agent, or Firm* — Wenderoth, Lind & Ponack, L.L.P.

(57) ABSTRACT

An object of the present invention is to provide an improved β-fructofuranosidase and a method for manufacturing the same. According to the present invention, there are provided an improved β-fructofuranosidase consisting of an amino acid sequence of a β-fructofuranosidase in which either or both of an amino acid corresponding to the $81^{st}$ position from an amino terminal of an amino acid sequence shown in SEQ ID NO: 1 and an amino acid corresponding to the $141^{st}$ position from the amino terminal of the amino acid sequence shown in SEQ ID NO: 1 is/are substituted with another amino acid/other amino acids, and a method for manufacturing the same. The improved β-fructofuranosidase of the present invention is advantageous in that it can produce trisaccharide FOS while suppressing the production of tetra- or higher-saccharide FOS, and thus can produce a FOS having improved crystallinity and hygroscopicity, and is also advantageous in that it can provide prebiotics having higher functionality.

15 Claims, 2 Drawing Sheets

Specification includes a Sequence Listing.

(56) References Cited

OTHER PUBLICATIONS

Yanai, Koji et al., "Molecular Cloning and Characterization of the Fructooligosaccharide-Producing β-Fructofuranosidase Gene from Aspergillus niger ATCC 20611", Biosci. Biotechnol. Biochem., 2001, vol. 65, No. 4, pp. 766-773.
Fujii, Tadashi et al., "Rapid evaluation of 1-kestose producing β-fructofuranosidases from *Aspergillus* species and enhancement of 1-kestose producing using a PgsA surface-display system", Biosci. Biotechnol., 2018, vol. 82, No. 9, p. 1599-1605.
Accession No. A0A4S3JXJ4, Database UniProtKB/TrEMBL [online], Definition: Uncharacterized protein, Aug. 12, 2020 [retrieved on Dec. 12, 2022].
Accession No. A0A5M9MM14, Database UniProtKB/TrEMBL [online], Definition: Uncharacterized protein, Aug. 12, 2020 [retrieved on Dec. 12, 2022].

* cited by examiner

β-FRUCTOFURANOSIDASE

CROSS-REFERENCE TO RELATED APPLICATION

The present application is a national stage entry from International Application No. PCT/JP2022/037083, filed on Oct. 4, 2022, and claims benefit of priority from Japanese Patent Application No. 2021-163489 filed on Oct. 4, 2021, the entire disclosures of which are incorporated herein by reference.

TECHNICAL FIELD

The present invention relates to an improved β-fructofuranosidase. The present invention also relates to a polynucleotide encoding the improved β-fructofuranosidase, a vector comprising the polynucleotide, and a transformant obtained by introducing the polynucleotide or the vector into a host. The present invention further relates to a method for manufacturing the improved β-fructofuranosidase, a method for manufacturing a fructooligosaccharide, and a method for manufacturing a 1-kestose crystal.

BACKGROUND ART

Since intestinal bacterial flora has a great influence on the health of humans, a health-promoting effect is exerted by improving the balance of microorganisms that make up the intestinal bacterial flora. Prebiotics refer to indigestible food ingredients that selectively promote the proliferation and activity of specific beneficial microorganisms such as bifidobacteria living in the intestinal environment. The prebiotics are known as more practical and efficient ways to manipulate the intestinal bacterial flora because the target bacteria already coexist within the intestines, unlike probiotics that change the intestinal bacterial flora upon intake of exogenous microorganisms (Non-Patent Document 1).

Fructooligosaccharides (FOSs) have a high function as prebiotics, and, among them, trisaccharide FOS, which has one fructose bonded to sucrose, is particularly useful. The trisaccharide FOS is known to be more effective in promoting the proliferation of bifidobacteria than tetra- or higher-saccharide FOS, and short-chain FOSs (a small number of fructoses bonded to sucrose) are more easily decomposed by microorganisms living in the intestines and are suitable as nutrient sources, and, as a result, contribute to providing a healthy composition of the intestinal bacterial flora (Non-Patent Document 2). On the other hand, β-fructofuranosidases, which produce FOSs, are widely present in plants, microorganisms, fungi and the like and vary in strength of enzyme activity depending on the type, and the FOSs to be produced are also different in length and production proportion accordingly (Non-Patent Documents 3 and 4). 0-Fructofuranosidases that produce the trisaccharide FOS are disclosed, for example, in Patent Documents 1 and 2.

REFERENCE LIST

Patent Documents

Patent Document 1: WO2015-99166
Patent Document 2: WO2016-143873

Non-Patent Documents

Non-Patent Document 1: Gibson G R, et al., J Nutr. 1995; 125(6):1401-1412.
Non-Patent Document 2: Tochio T, et al., Foods. 2018; 7(9):140.
Non-Patent Document 3: Hidaka H, et al., Agric Biol Chem. 1988; 52(5):1181-1187.
Non-Patent Document 4: Yanai K, et al., Biosci Biotechnol Biochem. 2001; 65(4):766-773.

SUMMARY OF THE INVENTION

While it is known that the FOSs produced by β-fructofuranosidases may include not only trisaccharide FOS but also tetra- and higher-saccharide FOSs, mixtures containing a plurality of types of FOSs (particularly, mixtures containing tetra- or higher-saccharide FOS) have the properties of poor crystallinity and high hygroscopicity. Therefore, there is a demand to increase the production proportion of a single type of FOS and improve crystallinity. It is also expected to increase the production proportion of trisaccharide FOS as a highly functional prebiotic. On the other hand, it has taken a great deal of effort and time to separate, remove, and reduce tetra- and higher-saccharide FOSs from mixtures containing a plurality of types of FOSs. An object of the present invention is to provide a novel improved β-fructofuranosidase to solve such problems.

The present inventors have found an improved β-fructofuranosidase having a high production proportion of trisaccharide FOS and a low production proportion of tetra- or higher-saccharide FOS by substituting an amino acid at a specific position of the amino acid sequence (SEQ ID NO: 1) of wild-type β-fructofuranosidase derived from *Aspergillus fijiensis* with a different amino acid. The present invention is based on this finding.

According to the present invention, the following inventions are provided.

[1] An improved β-fructofuranosidase consisting of an amino acid sequence of a β-fructofuranosidase in which either or both of an amino acid corresponding to the 81$^{st}$ position from an amino terminal of an amino acid sequence shown in SEQ ID NO: 1 and an amino acid corresponding to the 141$^{st}$ position from the amino terminal of the amino acid sequence shown in SEQ ID NO: 1 is/are substituted with another amino acid/other amino acids.

[2] The improved β-fructofuranosidase according to [1], wherein the 0-fructofuranosidase consists of an amino acid sequence having a sequence identity of 60% or more with the amino acid sequence of wild-type β-fructofuranosidase shown in SEQ ID NO: 1, and also having β-fructofuranosidase activity.

[3] The improved β-fructofuranosidase according to [1] or [2], which consists of either of the following amino acid sequences a) and b):

a) an amino acid sequence of a β-fructofuranosidase in which either or both of the amino acid (glycine (G)) corresponding to the 81$^{st}$ position from the amino terminal of the amino acid sequence shown in SEQ ID NO: 1 and the amino acid (leucine (L)) corresponding to the 141$^{st}$ position from the amino terminal of the amino acid sequence shown in SEQ ID NO: 1 is/are substituted with another amino acid/other amino acids; and b) an amino acid sequence in which one or more amino acids other than the glycine (G) at the 81$^{st}$ position and the leucine (L) at the 141$^{st}$ position is/are deleted, substituted, inserted, and/or added in the amino acid sequence a) above, and which has β-fructofuranosidase activity.

[4] The improved β-fructofuranosidase according to any one of [1] to [3], wherein the amino acid corresponding to the $81^{st}$ position from the amino terminal is substituted with an amino acid selected from the group consisting of aspartic acid (D), glutamic acid (E), phenylalanine (F), histidine (H), isoleucine (I), lysine (K), leucine (L), methionine (M), asparagine (N), glutamine (Q), arginine (R), serine (S), valine (V), tryptophan (W) and tyrosine (Y).

[5] The improved β-fructofuranosidase according to any one of [1] to [4], wherein the amino acid corresponding to the $141^{st}$ position from the amino terminal is substituted with an amino acid selected from the group consisting of alanine (A), aspartic acid (D), phenylalanine (F), glycine (G), isoleucine (I), lysine (K), asparagine (N), glutamine (Q), arginine (R), serine (S), threonine (T), tryptophan (W) and tyrosine (Y).

[6] A polypeptide comprising an enzymatically active portion of the amino acid sequence of the improved β-fructofuranosidase according to any one of [1] to [5], and having β-fructofuranosidase activity.

[7] A polynucleotide encoding the improved β-fructofuranosidase according to any one of [1] to [5] or the polynucleotide according to [6].

[8] An expression vector comprising the polynucleotide according to [7].

[9] A transformant obtained by introducing the polynucleotide according to [7] or the expression vector according to [8].

[10] The transformant according to [9], wherein the host is selected from the group consisting of bacteria, yeasts, molds and filamentous fungi.

[11] A method for manufacturing an improved β-fructofuranosidase, comprising the step of obtaining an improved β-fructofuranosidase from a culture of the transformant according to [9] or [10].

[12] A method for manufacturing a fructooligosaccharide, comprising the step of bringing the improved β-fructofuranosidase according to any one of [1] to [5], the polypeptide according to [6] or a culture of the transformant according to [9] or [10] into contact with sucrose.

[13] A method for manufacturing a 1-kestose crystal, comprising the steps of: manufacturing a fructooligosaccharide by carrying out the manufacture method according to [12]; and crystallizing the fructooligosaccharide.

The improved β-fructofuranosidase of the present invention is advantageous in that it can suppress the production of tetra- or higher-saccharide FOS, and thus can produce a FOS having improved crystallinity and hygroscopicity. The improved β-fructofuranosidase of the present invention is also advantageous in that it can produce trisaccharide FOS while suppressing the production of tetra- or higher-saccharide FOS, and thus can provide prebiotics having higher functionality.

DETAILED DESCRIPTION OF THE INVENTION

<<Definition>>

Figure 1:
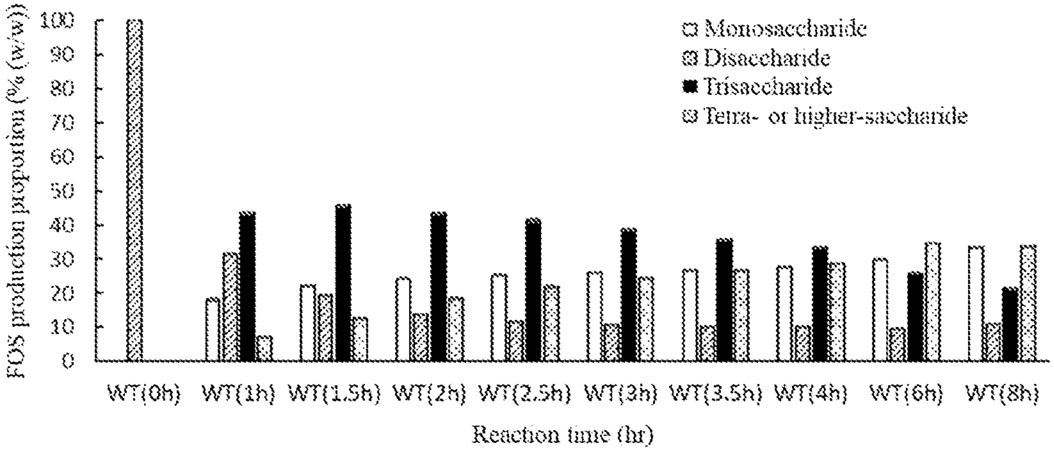
FIG. 1 shows the production proportions of FOSs (monosaccharide: glucose and fructose; disaccharide: sucrose; trisaccharide: trisaccharide FOS; and tetra- or higher-saccharide: tetra- or higher-saccharide FOS) at each reaction time by wild-type β-fructofuranosidase (WT).

In the present invention, the "fructooligosaccharide (sometimes abbreviated as "FOS" herein) refers to an oligosaccharide in which one to three molecules of fructose is/are bonded to sucrose. The FOS includes 1-kestose in which one fructose molecule is β-2,1-bonded to the fructose residue of sucrose (sometimes referred to as "GF2" or "trisaccharide FOS" herein); nystose in which two fructose molecules are β-2,1-bonded to the fructose residue of sucrose (sometimes referred to as "GF3" or "tetrasaccharide FOS" herein); and 1-fructofuranosyl-D-nystose in which three fructose molecules are β-2,1-bonded to the fructose residue of sucrose (sometimes referred to as "GF4" or "pentasaccharide FOS" herein). The FOS is synthesized by a β-fructofuranosidase.

In the present invention, the "β-fructofuranosidase" refers to an enzyme belonging to the GH32 family having sucrose hydrolyzing activity among the GH families (glycoside hydrolase families, which refer to groups of homologous proteins having a high sequence similarity among enzymes that hydrolyze glycosidic bonds of saccharides). An enzymatic reaction by a β-fructofuranosidase begins when sucrose enters a substrate binding pocket where a saccharide binds. A glycolysis reaction occurs, and the glycosidic bond between glucose and fructose is cleaved at the catalytic center site, so that glucose is liberated. The fructose portion forms an acyl enzyme intermediate with a catalytic group at the active center portion. Thereafter, fructose is liberated when water binds to the intermediate. At a high saccharide concentration, the transglycosylation activity is prioritized, and fructose forms a glycosidic bond with sucrose, which acts as an acceptor, to form trisaccharide FOS, which is liberated from the substrate binding pocket. Also, in the case where the acceptor saccharide is trisaccharide FOS, it forms a glycosidic bond with fructose and becomes tetrasaccharide FOS, which is liberated from the pocket. Through such an enzymatic reaction, FOSs with various lengths, such as tri-, tetra-, and penta-saccharides, are produced depending on the type of saccharide that serves as the acceptor. The term "β-fructofuranosidase" is sometimes used interchangeably with "β-fructofuranosidase," "fructosyltransferase," "fructosyltransferase," "saccharase," "β-D-fructofuranosidase," "β-D-fructofuranosidase," "invertase," "invertase," or "invertin," and all the terms have the same meaning.

<<Improved β-Fructofuranosidase>>

The improved β-fructofuranosidase of the present invention consists of an amino acid sequence of a β-fructofuranosidase to be improved in which either or both of amino acids at two specific positions is/are substituted with another amino acid/other amino acids. The amino acid/acids at specific position/positions to be substituted in the amino acid sequence of the β-fructofuranosidase can be specified by properly aligning the amino acid sequence of the β-fructofuranosidase to be improved with an amino acid sequence of SEQ ID NO: 1. Namely, it is possible to align the amino acid sequence of the β-fructofuranosidase to be improved with the amino acid sequence of SEQ ID NO: 1 using, for example, homology search software or program which will be described below to specify an amino acid corresponding to the 81$^{st}$ position from an amino terminal of the amino acid sequence of SEQ ID NO: 1 and an amino acid corresponding to the 141$^{st}$ position from an amino terminal of the amino acid sequence shown in SEQ ID NO: 1 as the amino acids at the specific positions to be substituted.

The improved β-fructofuranosidase of the present invention consists of an amino acid sequence of a β-fructofuranosidase to be improved in which either or both of an amino acid corresponding to the 81$^{st}$ position from an amino terminal of an amino acid sequence shown in SEQ ID NO: 1 and an amino acid corresponding to the 141$^{st}$ position from an amino terminal of an amino acid sequence shown in SEQ ID NO: 1 is/are substituted with an amino acid/amino acids which is/are different from the original amino acid/amino acids. The amino acid at the 81$^{st}$ position from the amino terminal of the amino acid sequence of SEQ ID NO: 1 is glycine (G), and the amino acid at the 141$^{st}$ position from the amino terminal of the amino acid sequence of SEQ ID NO: 1 is leucine (L). Therefore, the amino acid corresponding to the 81$^{st}$ position from the amino terminal of the amino acid sequence shown in SEQ ID NO: 1 is typically glycine (G), and the amino acid corresponding to the 141$^{st}$ position from the amino terminal of the amino acid sequence shown in SEQ ID NO: 1 is typically leucine (L). Namely, in the case where the amino acid sequence of the β-fructofuranosidase to be improved is composed of amino acids shown in SEQ ID NO: 1, the amino acid corresponding to the 81$^{st}$ position from the amino terminal is glycine (G), and the amino acid corresponding to the 141$^{st}$ position from the amino terminal is leucine (L).

The amino acid corresponding to the 81$^{st}$ position from the amino terminal of the amino acid sequence of SEQ ID NO: 1 can be substituted with an amino acid selected from the group consisting of 18 types of amino acids other than glycine (G) and cysteine (C) (alanine (A), aspartic acid (D), glutamic acid (E), phenylalanine (F), histidine (H), isoleucine (I), lysine (K), leucine (L), methionine (M), asparagine (N), glutamine (Q), arginine (R), serine (S), valine (V), tryptophan (W), tyrosine (Y), proline (P) and threonine (T)). From the viewpoint of increasing the production proportion of trisaccharide FOS or decreasing the production proportion of tetra- or higher saccharide FOS relative to that by wild type β-fructofuranosidase shown in SEQ ID NO: 1, the amino acid is preferably substituted with an amino acid selected from the group consisting of 15 types of amino acids other than glycine (G), cysteine (C), alanine (A), proline (P) and threonine (T) (aspartic acid (D), glutamic acid (E), phenylalanine (F), histidine (H), isoleucine (I), lysine (K), leucine (L), methionine (M), asparagine (N), glutamine (Q), arginine (R), serine (S), valine (V), tryptophan (W) and tyrosine (Y)). From the viewpoint of increasing the production proportion of trisaccharide FOS and decreasing the production proportion of tetra- or higher saccharide FOS relative to those by the wild type β-fructofuranosidase shown in SEQ ID NO: 1, the amino acid is more preferably substituted with an amino acid selected from the group consisting of phenylalanine (F), histidine (H), isoleucine (I), lysine (K), leucine (L), methionine (M), asparagine (N), glutamine (Q), arginine (R), serine (S), valine (V), tryptophan (W) and tyrosine (Y). From the viewpoint of increasing the production proportion of trisaccharide FOS to more than 50% and setting the production proportion of tetra- or higher-saccharide FOS to less than 10%, the amino acid is even more preferably substituted with an amino acid selected from the group consisting of lysine (K), leucine (L), tryptophan (W) and tyrosine (Y). From the viewpoint of increasing the production proportion of trisaccharide FOS to more than 55% and setting the production proportion of tetra- or higher-saccharide FOS to less than 8%, the amino acid is particularly preferably substituted with tryptophan (W) or tyrosine (Y). Here, the production proportion of trisaccharide FOS or tetra- or higher-saccharide refers to the proportion thereof to all saccharides contained in a reaction sample after an enzymatic reaction. It can be evaluated according to the descriptions in Example 1, item (1) c (i) and item (2) in the Examples which will be described below (the same applies hereinafter in the present specification).

The amino acid corresponding to the 141$^{st}$ position from the amino terminal of the amino acid sequence of SEQ ID NO: 1 can be substituted with an amino acid selected from the group consisting of 18 types of amino acids other than leucine (L) and cysteine (C) (alanine (A), aspartic acid (D), glutamic acid (E), phenylalanine (F), glycine (G), histidine (H), isoleucine (I), lysine (K), methionine (M), asparagine (N), glutamine (Q), arginine (R), serine (S), threonine (T), valine (V), tryptophan (W), tyrosine (Y) and proline (P)). From the viewpoint of increasing the production proportion of trisaccharide FOS or decreasing the production proportion of tetra- or higher saccharide FOS relative to that of the wild type β-fructofuranosidase shown in SEQ ID NO: 1, the amino acid is preferably substituted with an amino acid selected from the group consisting of 13 types of amino acids other than leucine (L), cysteine (C), glutamic acid (E), histidine (H), methionine (M), valine (V) and proline (P) (alanine (A), aspartic acid (D), phenylalanine (F), glycine (G), isoleucine (I), lysine (K), asparagine (N), glutamine (Q), arginine (R), serine (S), threonine (T), tryptophan (W) and tyrosine (Y)). From the viewpoint of increasing the production proportion of trisaccharide FOS and decreasing the production proportion of tetra- or higher saccharide FOS relative to those of the wild type β-fructofuranosidase shown in SEQ ID NO: 1, the amino acid is more preferably substituted with an amino acid selected from the group consisting of alanine (A), aspartic acid (D), phenylalanine (F), glycine (G), isoleucine (I), lysine (K), asparagine (N), arginine (R), serine (S), threonine (T), tryptophan (W) and tyrosine (Y). From the viewpoint of increasing the production proportion of trisaccharide FOS to more than 47% and decreasing the production proportion of tetra- or higher-saccharide FOS to less than 16%, the amino acid is even more preferably substituted with an amino acid selected from the group consisting of alanine (A), aspartic acid (D), isoleucine (I), lysine (K), arginine (R), threonine (T) and tryptophan (W). From the viewpoint of increasing the production proportion of trisaccharide FOS to more than 49% and decreasing the production proportion of tetra- or higher-saccharide FOS to less than 13%, the amino acid is particularly preferably substituted with lysine (K) or tryptophan (W).

The β-fructofuranosidase to be improved can consist of an amino acid sequence having a sequence identity of 60% or more (preferably, 65% or more, 70% or more, 75% or more, 80% or more, 85% or more, 90% or more, 93% or more, 95% or more, 98% or more, or 99% or more) with the amino acid sequence of the wild-type β-fructofuranosidase shown in SEQ ID NO: 1. Here, the "identity" refers to the degree of identity when the sequences to be compared with each other are properly aligned, and means the appearance rate (%) of exact amino acid matches between the sequences. For example, the presence of gaps in the sequence and the properties of the amino acids are taken into consideration in the calculation of the identity (Wilbur, Natl. Acad. Sci. U.S.A. 80: 726-730 (1983)). The above alignment can be performed, for example, by utilizing any algorithm, and, specifically, publicly available homology search software such as BLAST (Basic local alignment search tool) (Altschul et al., J. Mol. Biol. 215:403-410 (1990)), FASTA (Peasron et al., Methods in Enzymology 183: 63-69 (1990)) or Smith-Waterman (Meth. Enzym., 164, 765 (1988)) can be used. Furthermore, the identity can be calculated using, for example, the publicly available homology search program as indicated above, and can be calculated using, for example, a default parameter in the homology algorithm BLAST (blast.ncbi.nlm.nih.gov) from the National Center for Biotechnology Information (NCBI).

The improved β-fructofuranosidase to be improved consists of an amino acid sequence having a sequence identity of 60% or more with the amino acid sequence of the wild-type β-fructofuranosidase shown in SEQ ID NO: 1, and also having β-fructofuranosidase activity. In this case, the phrase "having β-fructofuranosidase activity" means that the amino acid sequence involved can be defined as having about 70% or more activity, about 80% or more activity, about 90% or more activity, about 95% or more activity or about 100% or more activity relative to the activity of the wild-type β-fructofuranosidase consisting of the amino acid sequence shown in SEQ ID NO: 1 under conditions of a temperature of 50 to 55° C. and a pH of 5.5. The β-fructofuranosidase activity can be evaluated, for example, as follows: a solution containing the protein or polypeptide to be measured and a solution containing sucrose are mixed together; the mixed solution is incubated; and the amount of glucose produced by an enzymatic reaction is measured using high performance liquid chromatography (HPLC), thin layer chromatography (TLC), various glucose quantification kits, and the like; and the β-fructofuranosidase activity is evaluated from the value obtained in the measurement and the amount of the enzyme used in the reaction.

The β-fructofuranosidase to be improved is typically a wild-type enzyme, for example, can be derived from any of organisms such as microorganisms, fungi and plants, and can be preferably derived from a microorganism belonging to the genus *Aspergillus*. However, in the present invention, the use of a β-fructofuranosidase into which an artificial mutation has been introduced as a target to be improved would not be precluded.

Examples of β-fructofuranosidases derived from microorganisms belonging to the genus *Aspergillus* include those indicated in Table 1. In the amino acid sequences of the β-fructofuranosidases indicated in Table 1, the presence of the amino acid corresponding to the 81$^{st}$ position from the amino terminal of the amino acid sequence shown in SEQ ID NO: 1 and the amino acid corresponding to the 141$^{st}$ position from the amino terminal of the amino acid sequence shown in SEQ ID NO: 1 was confirmed.

TABLE 1

Examples of β-fructofuranosidases derived from microorganisms (bacterial species) belonging to the genus *Aspergillus*, having sequence identity of 60% or more with amino acid sequence of wild-type β-fructofuranosidase shown in SEQ ID NO: 1

| Bacterial species (origin) | Accession No. | Sequence Identity (%) |
|---|---|---|
| *Aspergillus aculeatus* | ANF99482.1 | 99.69 |
| *Aspergillus japonicus* | 3LF7_A | 99.53 |
| *Aspergillus japonicus* | ADK46938.1 | 99.39 |
| *Aspergillus japonicus* | 3LDK_A | 99.37 |
| *Aspergillus fijiensis* CBS 313.89 | XP_040799211.1 | 99.08 |
| *Aspergillus brunneoviolaceus* CBS 621.78 | XP_025443891.1 | 98.47 |
| *Aspergillus aculeatinus* CBS 121060 | XP_025508898.1 | 97.40 |
| *Aspergillus japonicus* | ABD97344.1 | 97.40 |
| *Aspergillus aculeatus* ATCC 16872 | XP_020051300.1 | 96.18 |
| *Aspergillus uvarum* CBS 121591 | XP_025487796.1 | 93.10 |
| *Aspergillus indologenus* CBS 114.80 | PYI32185.1 | 92.98 |
| *Aspergillus japonicus* CBS 114.51 | XP_025532678.1 | 91.85 |
| *Aspergillus violaceofuscus* CBS 115571 | PYI19045.1 | 90.37 |
| *Aspergillus homomorphus* CBS 101889 | XP_025551517.1 | 83.78 |
| *Aspergillus saccharolyticus* JOP 1030-1 | XP_025428139.1 | 81.69 |
| *Aspergillus costaricaensis* CBS 115574 | XP_025540508.1 | 64.98 |
| *Aspergillus luchuensis* IFO 4308 | 5XH8_A | 64.61 |
| *Aspergillus ellipticus* CBS 707.79 | PYH88239.1 | 64.49 |
| *Aspergillus niger* | AHC54391.1 | 63.94 |
| *Aspergillus costaricaensis* CBS 115574 | XP_025540508.1 | 63.94 |

According to a preferred aspect of the present invention, there is provided an improved β-fructofuranosidase consisting of either of the amino acid sequences a) and b) according to [3] above. The type of the amino acid to be substituted in the amino acid sequence a) and the type of the amino acid after substitution are as described above. The amino acid sequence b) may have a modification selected from the group consisting of deletion(s), substitution(s), insertion(s), and addition(s) in one or more amino acids other than glycine (G) at the 81$^{st}$ position and leucine (L) at the 141$^{st}$ position. The number of amino acids to be modified can be, for example, 1 to 65, 1 to 50, 1 to 40, 1 to 30, or 1 to 20, and is preferably 1 to 10, more preferably 1 to 6, and particularly preferably 1 to several, 1 to 4, 1 to 3, 1 to 2, or 1. The number of amino acids to be modified can also be the number of mutations that occur by known methods such as site mutagenesis, or the number of mutations that occur naturally. The modification may also be a plurality of homologous modifications (e.g., a plurality of substitutions) or a plurality of heterologous modifications (e.g., a combination of one or more deletions and one or more substitutions).

The amino acid sequence b) can also be an amino acid sequence having a sequence identity of 80% or more (preferably 85% or more, 90% or more, 93% or more, 95% or more, 98% or more, or 99% or more) with the amino acid sequence a) and also having β-fructofuranosidase activity. However, also in this case, the amino acid sequence b) will have a modification selected from the group consisting of deletion(s), substitution(s), insertion(s), and addition(s) in one or more amino acids other than glycine (G) at the $81^{st}$ position and leucine (L) at the $141^{st}$ position.

The modification of the amino acid in the amino acid sequence b) may be a conservative modification (e.g., conservative mutation). The "conservative modification" or "conservative mutation" means modifying or mutating one or more amino acids, without substantially modifying the function of the protein. The substitution of the amino acid may also be a conservative substitution. The "conservative substitution" means substituting one or more amino acids with another amino acid/other amino acids, without substantially modifying the function of the protein. In the conservative substitution, the amino acid to be substituted and the amino acid after substitution are preferably similar in properties and/or function, for example. Specifically, they are preferably similar in chemical properties such as hydrophobicity and hydrophilicity indexes, polarity and charge, or physical properties such as secondary structure. Amino acids or amino acid derivatives having similar properties and/or functions in this manner are known in the art. For instance, examples of non-polar amino acids (hydrophobic amino acids) include alanine, valine, isoleucine, leucine, proline, tryptophan, phenylalanine and methionine. Examples of polar amino acids (neutral amino acids) include glycine, serine, threonine, tyrosine, glutamine, asparagine and cysteine. Examples of amino acids having a positive charge (basic amino acids) include arginine, histidine and lysine, and examples of amino acids having a negative charge (acidic amino acids) include aspartic acid and glutamic acid.

Also, the amino acid sequence b) consists of an amino acid sequence having a modification selected from the group consisting of deletion(s), substitution(s), insertion(s), and addition(s) in one or more amino acids other than glycine (G) at the $81^{st}$ position and leucine (L) at the $141^{st}$ position, and also having β-fructofuranosidase activity. In this case, the phrase "having β-fructofuranosidase activity" means that the amino acid sequence involved can be defined as having about 90% or more activity, about 95% or more activity, about 98% or more activity, or about 100% or more activity relative to the activity of the β-fructofuranosidase consisting of the amino acid sequence a) under conditions of a temperature of 50 to 55° C. and a pH of 5.5. The β-fructofuranosidase activity can be measured in the same manner as described above.

The improved β-fructofuranosidase of the present invention can be obtained, for example, by a chemical synthesis method or a gene recombination technique. In the chemical synthesis method, the improved β-fructofuranosidase of the invention can be synthesized, for example, based on amino acid sequence information, according to the chemical synthesis method such as an Fmoc method (fluorenylmethyloxycarbonyl method), a tBoc method (t-butyloxycarbonyl method) or a cell-free protein synthesis method. The improved β-fructofuranosidase of the present invention can also be synthesized using a commercially available peptide synthesizer.

The improved β-fructofuranosidase of the present invention can be manufactured by culturing a genetically modified microorganism having the ability to produce it. For example, the improved β-fructofuranosidase of the present invention can be obtained by introducing a polynucleotide encoding the improved β-fructofuranosidase of the present invention into an appropriate host to obtain a transformant, culturing the transformant, and extracting the improved β-fructofuranosidase from a culture of the transformant. Specifically, it can be obtained according to the descriptions in the Examples (for example, Example 1, item (1) a and b) which will be described below.

The polynucleotide encoding the improved β-fructofuranosidase of the present invention can be synthesized using various commercially available polynucleotide synthesizers, and, additionally, can also be obtained by site-specific mutagenesis using an inverse polymerase chain reaction (PCR), as will be described in Examples 1 and 2 below. The "polynucleotide" includes DNA and RNA, as well as modified products thereof and artificial nucleic acids, but is preferably DNA. Furthermore, the DNA includes cDNA, genomic DNA, and chemically synthesized DNA.

<<Polypeptide Containing Enzymatically Active Portion of Improved (3-fructofuranosidase>>

According to the present invention, there is provided a polypeptide comprising an enzymatically active portion of the amino acid sequence of the improved β-fructofuranosidase of the present invention and having β-fructofuranosidase activity. The amino acid sequence of the polypeptide of the present invention typically comprises at least a site (region) having β-fructofuranosidase activity. In the improved β-fructofuranosidase of the present invention, examples of the site having β-fructofuranosidase activity include a site corresponding to the $20^{th}$ to $654^{th}$ (region excluding a signal sequence on the N-terminal side) positions from the amino terminal of the amino acid sequence shown in SEQ ID NO: 1; a site corresponding to the $50^{th}$ to $558^{th}$ (region characteristic of enzymes belonging to the glycosyl hydrolase family 32) positions from the amino terminal of the amino acid sequence shown in SEQ ID NO: 1; a site corresponding to the $59^{th}$ to $428^{th}$ (region characteristic of the N-terminal side sequence of the enzymes belonging to the glycosyl hydrolase family 32) positions from the amino terminal of the amino acid sequence shown in SEQ ID NO: 1; a site corresponding to the $60^{th}$ (catalytic center amino acid Asp60) position from the amino terminal of the amino acid sequence shown in SEQ ID NO: 1; a site corresponding to the $191^{st}$ (catalytic center amino acid Asp191) position from the amino terminal of the amino acid sequence shown in SEQ ID NO: 1; and a site corresponding to the $292^{nd}$ (catalytic center amino acid Glu292) position from the amino terminal of the amino acid sequence shown in SEQ ID NO: 1. The polypeptide of the present invention can be obtained by the same method as the method for obtaining the improved 3-fructofuranosidase of the present invention.

<<Polynucleotide Encoding Improved β-Fructofuranosidase or the Like, and Vector Comprising Same>>

According to the present invention, there is provided a polynucleotide encoding the improved β-fructofuranosidase of the present invention or the polypeptide of the present invention. The polynucleotide of the present invention can be obtained using, for example, the polynucleotide synthesis method described for the method for obtaining the improved β-fructofuranosidase of the present invention.

According to the present invention, there is also provided a recombinant vector comprising a polynucleotide encoding an improved β-fructofuranosidase.

The recombinant vector of the present invention can be obtained by operably linking the polynucleotide encoding the improved β-fructofuranosidase of the present invention to a vector. The linking of the polynucleotide to the vector can be performed according to a conventional method, and, for example, can be performed by ligating the polynucleotide and a polynucleotide of a linearized vector, as will be described in the Examples (Example 1, item (1) a) below. Examples of the vector can include phage vector, plasmid vector, cosmid and phagemid, and can be appropriately selected depending on the host, operability and the like. Also, the recombinant vector of the present invention may comprise, in addition to the polynucleotide encoding the improved β-fructofuranosidase of the present invention, a selection marker gene for a transformant such as a drug resistance marker gene or an auxotrophic marker gene; a promoter necessary for expression of the improved β-fructofuranosidase; a transcriptional regulatory signal or translational regulatory signal such as a transcription start signal, a ribosome binding site, a translation stop signal or a transcription termination signal; and the like.

<<<Transformant>>

According to the present invention, there is provided a transformant capable of producing the improved β-fructofuranosidase of the present invention or the polypeptide of the present invention. The transformant of the present invention can be obtained by introducing the polynucleotide encoding the improved β-fructofuranosidase of the present invention or the polypeptide of the present invention, or the recombinant vector of the present invention into a host. Here, examples of the host can include bacteria such as *Escherichia coli* (*E. coli*) and *Bacillus subtilis*, yeasts, molds, and filamentous fungi, and can be appropriately selected depending on the type, operability and the like of the recombinant vector. The introduction (transformation) of the DNA or recombinant vector into the host can be performed according to a conventional method. Additionally, a homologous recombination method or the like can be used to directly introduce the DNA of interest into the chromosomes of the host.

<<<Method for Manufacturing Improved β-Fructofuranosidase>>

According to the present invention, there is provided a method for manufacturing the improved β-fructofuranosidase of the present invention or the polypeptide of the present invention. The manufacture method of the present invention can be carried out by culturing the transformant of the present invention in a medium suitable for culturing the transformant, and optionally collecting the improved β-fructofuranosidase or polypeptide of the present invention from a culture of the transformant obtained by culture. The medium used in the culture is not particularly limited as long as it is a nutrient medium in which the transformed microorganism can grow and the improved β-fructofuranosidase of the present invention or the polypeptide of the present invention can be produced, and either a synthetic medium or a natural medium may be used. In addition, as culturing conditions such as time and temperature, conditions suitable for the microorganism to be cultured can be appropriately selected.

In the manufacture method of the present invention, the culture obtained by culturing the transformant may be obtained as the improved β-fructofuranosidase of the present invention or the polypeptide of the present invention as it is, and the improved β-fructofuranosidase of the present invention or the polypeptide of the present invention can also be isolated and purified from the culture.

To obtain the culture obtained by culturing the transformant as the improved β-fructofuranosidase of the present invention or the polypeptide of the present invention as it is, for example, the polynucleotide or recombinant vector is designed so that the protein to be expressed is expressed on the cell surface or inside the cells of the transformant; the culture is centrifuged to collect the transformant; and this transformant can be obtained as the improved β-fructofuranosidase of the present invention or the polypeptide of the present invention as it is. Alternatively, the collected transformant is crushed, and the crushed product can also be obtained as the improved β-fructofuranosidase of the present invention or the polypeptide of the present invention.

The isolation and purification of the improved β-fructofuranosidase of the present invention or the polypeptide of the present invention from the culture can be performed, for example, by designing the polynucleotide or recombinant vector so that the expressed protein is secreted to the outside of the transformant, and centrifuging the culture to collect a culture supernatant. The improved β-fructofuranosidase of the present invention or the polypeptide of the present invention can be purified by designing the polynucleotide or recombinant vector so that the protein to be expressed is expressed inside the transformant, centrifuging the culture to collect a precipitated transformant, crushing this transformant through suspension in a buffer, freezing/thawing, ultrasonication, grinding or the like, and then centrifuging the crushed product to collect a supernatant. Examples of other purification methods include methods of subjecting the supernatant of the culture solution or the crushed product to heat treatment, salt precipitation, solvent precipitation, dialysis, ultrafiltration, gel filtration, SDS-polyacrylamide gel electrophoresis, ion exchange chromatography, affinity chromatography, hydrophobic chromatography, reversed-phase chromatography, and isoelectric focusing.

<<<Method for Manufacturing Improved Fructooligosaccharide>>

According to the present invention, a method for manufacturing an improved fructooligosaccharide is provided. The method for manufacturing a fructooligosaccharide according to the present invention comprises the step of bringing the improved β-fructofuranosidase of the present invention, the polypeptide of the present invention or a culture of the transformant of the present invention into contact with sucrose.

In the method for manufacturing a fructooligosaccharide according to the present invention, the contact between the improved β-fructofuranosidase of the present invention or the like and sucrose can be performed, for example, by adding the improved β-fructofuranosidase or the like to a solution containing sucrose, followed by incubation. As incubation conditions, for example, the temperature can be 20 to 60° C., preferably 25 to 55° C., more preferably 30 to 50° C., and even more preferably 40 to 50° C., and the time can be 1 to 20 hours, preferably 1 to 8 hours, and more preferably 2 to 4 hours. The contact between the culture obtained by culturing the transformant of the present invention and sucrose can be performed similarly. The culture of the present invention may be a culture subjected to some treatment such as crushing, grinding, suspension in a buffer, freezing/thawing, ultrasonication, centrifugation, heat treatment, salt precipitation, solvent precipitation, dialysis, ultrafiltration, gel filtration, SDS-polyacrylamide gel electrophoresis, ion exchange chromatography, affinity chromatography, hydrophobic chromatography, reversed-phase chromatography, isoelectric focusing or the like, or may be a culture not subjected to any treatment.

The method for manufacturing a fructooligosaccharide according to the present invention can also comprise an optional additional step, and can comprise, for example, any of a fructooligosaccharide separation step by chromatography, a crystallization step, a drying step, a washing step, a filtration step, a sterilization step, and a step of adding a food additive, or a combination of some or all of the steps.

<<<Method for Manufacturing 1-Kestose Crystal>>

According to the present invention, a method for manufacturing a 1-kestose crystal is provided. The method for manufacturing 1-kestose according to the present invention is characterized by using a fructooligosaccharide manufactured by the method for manufacturing a fructooligosaccharide according to the present invention. The method for manufacturing a 1-kestose crystal according to the present invention comprises the steps of manufacturing a fructooligosaccharide by bringing the improved β-fructofuranosidase of the present invention, the polypeptide of the present invention or a culture of the transformant of the present invention into contact with sucrose; and crystallizing the fructooligosaccharide. The step of manufacturing a fructooligosaccharide can be carried out according to the descriptions about the improved β-fructofuranosidase of the present invention and the method for manufacturing the same, as well as the method for manufacturing a fructooligosaccharide according to the present invention. The step of crystallizing the fructooligosaccharide can be carried out according to a conventional method.

EXAMPLES

Hereinafter, the present invention will be described in more detail by way of the following examples, but is not limited to these examples.

Example 1: Review on Wild-Type β-Fructofuranosidase

In Example 1, the amounts of FOSs produced were reviewed using wild-type β-fructofuranosidase.

(1) Method a. Preparation of Plasmid of Wild-Type β-Fructofuranosidase

The preparation of a plasmid into which the gene of wild-type β-fructofuranosidase derived from *Aspergillus fijiensis* (*Aspergillus fijiensis* ATCC20611) (sometimes referred to as "WT-AfBFFase" or "WT" herein) was inserted was performed by the following procedures. The amino acid sequence (SEQ ID NO: 1) of WT-AfBFFase is indicated in Table 2.

TABLE 2

| Amino acid sequence (SEQ ID NO: 1) of WT-AfBFFase |
|---|
| MKLTTTTLALATGAAAAEASYHLDTTAPPPTNLSTLPNNTLFHVW<br>RPRAHILPAEGQIGDPCAHYTDPSTGLFHVGFLHDGDGIAGATTA<br>NLATYTDTSDNGSFLIQPGGKNDPVAVFDGAVIPVGVNNTPTLLY<br>TSVSFLPIHWSIPYTRGSETQSLAVARDGGRRFDKLDQGPVIADH<br>PFAVDVTAFRDPFVFRSAKLDVLLSLDEEVARNETAVQQAVDGWT<br>EKNAPWYVAVSGGVHGVGPAQFLYRQNGGNASEFQYWEYLGEWWQ<br>EATNSSWGDEGTWAGRWGFNFETGNVLFLTEEGHDPQTGEVFVTL<br>GTEGSGLPIVPQVSSIHDMLWAAGEVGVGSEQEGAKVEFSPSMAG<br>FLDWGFSAYAAAGKVLPASSAVSKTSGVEVDRYVSFVWLTGDQYE<br>QADGFPTAQQGWTGSLLLPRELKVQTVENVVDNELVREEGVSWVV<br>GESDNQTARLRTLGITARETKAALLANGSVTAEEDRTLQTAAVVP<br>FAQSPSSKFFVLTAQLEFPASARSSPLQSGEFILASELERTAIYY<br>QFSNESLVVDRSQTSAAAPTNPGLDSFTESGKLRLDVIENGQEQV<br>ETLDLTVVVDNAVVEVYANGRFALSTWARSWYDNSTQIRFFHNGE<br>GEVQFRNVSVSEGLYNAWPERN |

(i) PCR

A restriction enzyme treatment site was added to the WT-AfBFFase gene using the PCR method. Table 3 indicates the primers used, Table 4 indicates the PCR composition, and Table 5 indicates the PCR conditions. The template DNA used was obtained by removing, from the amino acid sequence shown in SEQ ID NO: 1, the site corresponding to the signal sequence (amino acids at the 1st to 19th positions, the underlined portion of the amino acid sequence indicated in Table 2).

TABLE 3

| Primer base sequence | |
|---|---|
| Oligo DNA | Base sequence |
| AfBFFase Fw (SEQ ID NO: 2) | attataGGATCCTCCTACCAT TTGGATACGACTGCACCACCG |
| AfBFFase Rv (SEQ ID NO: 3) | attataCTCGAGTTATCAGTTG CGCTCAGGCCACGCGTTATATA A |

TABLE 4

| PCR composition | |
|---|---|
| Composition | Total amount 25 μL |
| Template DNA | 1 ng |
| 10 × KOD Plus ver | 2.5 μL |
| 2 mM dNTP | 2.5 μL |
| 25 mM $MgSO_4$ | 1.5 μL |
| Forward primer | 1.5 μL |
| Reverse primer | 1.5 μL |
| Purified water ($ddH_2O$) | Remaining amount |

TABLE 5

| PCR conditions | | |
|---|---|---|
| Temperature | Time (min) | Number of cycles |
| 95 °C | 2 | 1 |
| 96 °C | 1 | 25 or 50 |
| 55 °C | 1 | |
| 72 °C | 2 | |
| 72 °C | 7 | 1 |
| 8 °C | retained | |

(ii) Gel Extraction of PCR Product

The PCR product amplified in (i) above and Midori Green Direct (NIPPON Genetics Co., Ltd.) were mixed at a ratio of 5:1, and electrophoresis was performed on a 1% agarose gel (0.5×TAE buffer: Tris-HCl (20 mM), acetic acid (10 mM), EDTA (0.5 mM), pH 8.0). After the electrophoresis, a green-emitting LED was applied to the gel and a band of interest was cut out. DNA was then extracted using FastGene Gel/PCR Extraction Kit (NIPPON Genetics Co., Ltd.).

(iii) Restriction Enzyme Treatment

According to the descriptions of Gilbreth R N et al., Proc Natl Acad Sci USA. 2011; 108(19): 7751-6. and Koide A et al., Proc Natl Acad Sci USA. 2007; 104(16):6632-7, a pHFT2 vector was prepared based on a pET28a vector (Novagen). The pHFT2 vector is resistant to kanamycin, and 10×His and a TEV protease cleavage site are added to the N-terminal sequence. Next, the pHFT2 vector was subjected to restriction enzyme treatment with the composition indicated in Table 6. In addition, the DNA gel-extracted in (ii) above was subjected to restriction enzyme treatment with the composition indicated in Table 7. Both the restriction enzyme treatments were performed under conditions of 37° C., 1 hour and still-standing.

TABLE 6

| Composition of restriction enzyme treatment of pHFT2 vector | |
|---|---|
| Composition | Total amount 50 μL |
| DNA (pHFT2 vector) | 1 μg |
| 10 × Cut Smart | 5 μL |
| BamHI (restriction enzyme) | 0.25 μL |
| XhoI (restriction enzyme) | 0.5 μL |
| Purified water (ddH$_2$O) | Remaining amount |

TABLE 7

| Composition of restriction enzyme treatment of gel-extracted DNA | |
|---|---|
| Composition | Total amount 50 μm |
| DNA (PCR product) | 45 μL |
| 10 × Cut Smart | 5 μL |
| BamHI | 0.5 μL |
| XhoI | 0.5 μL |
| Purified water (ddH$_2$O) | Remaining amount |

(iv) Gel Extraction of Restriction Enzyme-Treated Vector and Insert DNA

The vector and insert DNA restriction enzyme-treated in (iii) above were gel-extracted in the same manner as described in (ii) above.

(v) Ligation

The vector and insert DNA obtained in (iv) above were mixed so that the molar ratio was 1:8, 5 μL of Ligation-Convenience Kit (NIPPON GENE CO., LTD.) was added to 5 μL of the mixed solution, and the mixture was reacted at 16° C. for 15 minutes.

(vi) Transformation of *E. coli* JM109

To *E. coli* JM109 (NIPPON GENE CO., LTD.) (competent cell), 10 L of the ligation solution reacted in (v) above was added, and allowed to stand on ice. Thereafter, the solution was incubated at 42° C. for 45 to 50 seconds and immediately allowed to stand on ice. After the elapse of 3 minutes, an SOC medium was added to achieve a 10-fold dilution, and recovery culture was performed at 37° C. and 120 rpm for 1 hour. After culture, the culture solution was centrifuged at 5,000×g for 30 seconds, the supernatant was removed, and the culture solution was concentrated to 100 μL. The concentrated solution was seeded on an LB medium plate (containing kanamycin (50 g/mL)) and cultured overnight at 37° C. Colonies generated through transformation were inoculated into a 2XYT liquid medium (containing kanamycin (50 g/mL)) and cultured overnight. The culture solution was subjected to plasmid extraction using FastGene Plasmid Mini Kit (NIPPON Genetics Co., Ltd.). It was confirmed by DNA sequencing service (Eurofins) that the WT-AfBFFase gene was incorporated into the pHFT2 vector.

b. Protein Expression and Purification (i) Transformation and Culture of *E. coli* BL21 (DE3)

*E. coli* BL21 (DE3) was transformed using 2 μL of the plasmid into which the WT-AfBFFase gene prepared in item (1) above (sometimes referred to as "pHFT2_WT-AfBFFase" herein) was incorporated, and the transformed *E. coli* BL21 was seeded on a kanamycin plate. The transformation was performed in the same manner as described in item (1) a (vi) above. After overnight culture at 37° C., single colonies on the plate were inoculated into 5 mL of an LB liquid medium (containing kanamycin (50 g/mL)) and cultured at 37° C. and 120 rpm for 16 hours. Then, 5 mL of the preculture solution was inoculated into 500 mL of a 2XYT medium (containing kanamycin (50 g/mL)), and cultured at 37° C. until the turbidity reached 0.3 to 0.5. Thereafter, IPTG (final concentration: 0.2 mM) was added and cultured with shaking at 18° C. for 16 hours. The culture solution was centrifuged at 8000 g for 10 minutes to collect bacteria. After collection of bacteria, the bacterial cells were suspended in and washed with NaCl (150 mM), centrifugation was performed again, and the precipitated bacterial cells were cryopreserved at −30° C.

(ii) Purification by Affinity Chromatography

The precipitated bacterial cells were suspended in 15 mL of a crushing buffer (NaCl (500 mM), Tris-HCl (20 mM), imidazole (20 mM), pH 8.0) and subjected to ultrasonic crushing. After crushing for 30 seconds, 10 sets, in total, of 1-minute ice cooling defined as one set were performed. A cell-free extract was obtained by centrifuging the crushed solution at 1800×g and 4° C. for 30 minutes and filtering the solution through a 0.45-am sterile filter. Imidazole was added to the extract so as to attain a final concentration of 20 mM, and the mixture was subjected to a His Trap HP column. It was washed with a His TrapA buffer (NaCl (500 mM), Tris-HCl (20 mM), imidazole (20 mM), pH 8.0), and, subsequently, a His TrapB buffer (imidazole (500 mM), NaCl (500 mM), a Tris-HCl buffer (50 mM), pH 8.0) was added to elute it with a concentration gradient of 4 to 100%. The eluted protein solution of interest was concentrated to 2.5 mL at 4000×g using a 50-kDa Vivaspin Turbo 30 centrifugal ultrafiltration filter.

(iii) Purification by Gel Filtration Chromatography

In order to remove aggregates that could not be separated using the His Trap HP column, purification was performed by gel filtration chromatography. Using a gel filtration buffer (NaCl (150 mM), Tris-HCl (50 mM), pH 8.0), the protein solution was subjected to a HiLoad 16/60 Superdex 200 prep grad column (120 mL, GE HealthCare). A fraction containing the respective proteins was collected, concentrated using a 50-kDa Vivaspin Turbo 3010 centrifugal ultrafiltration filter, and stored at 4° C. as a purified solution. The concentration of the purified solution was measured at an absorbance of 280 nm. Also, the absorbance coefficient (Abs 0.1% (=1 g/L)) of WT-AfBFFase is 1.747.

(iv) SDS-PAGE

The purified protein solution was applied to the 10% (w/v) polyacrylamide gel prepared to perform electrophoresis. Protein Molecular Weight Marker Broad (Takara Bio Inc.) was used as a molecular weight marker. Through the procedures, it was confirmed that the proteins of interest had been purified.

c. Evaluation of Amount of FOS Produced (i) Enzymatic Reaction

The reaction was started by mixing a substrate solution (1 M sucrose) and the purified protein solution (containing WT-AfBFFase (1 g) obtained in item (1) b above, which was prepared with an analysis buffer (50 mM sodium phosphate buffer, pH 5.5)). The sample was reacted at 50° C., collected at 0 hours, 1 hour, 1.5 hours, 2 hours, 2.5 hours, 3 hours, 3.5 hours, 4 hours, 6 hours, and 8 hours and boiled for 15 minutes, and the reaction was stopped. The same operation was performed three times at the respective reaction times. The sample solution after the reaction was stored at −20° C.

(ii) Liquid Chromatography (HPLC) Analysis

The amounts of monosaccharides, disaccharides, and FOSs produced were analyzed by hydrophobic interaction chromatography. The amounts were measured using an ULTRON AF-HILIC-CD column (Shimadzu Corporation)

of HPLC (LC-20AD, Shimadzu Corporation). In addition, 74.1% acetonitrile was used as the analysis buffer. As the saccharide chain becomes longer, the degree of hydrophobicity increases, and thus the retention time is prolonged. This difference in retention time was used for detection using a differential refractive index detector (RID). The elution time varies depending on the length of the saccharide, and the amounts of the saccharides produced can be calculated from the peak area. Thus, a calibration curve was created using a known saccharide. This calibration curve was used to calculate the amounts of FOSs produced.

(2) Result

The results were as shown in Table 8 and FIG. 1. Through the enzymatic reaction, it was confirmed that the disaccharide (sucrose) accounted for 100% of the total saccharide before the reaction, but that, with the elapse of the reaction time, the disaccharide was consumed, leading to a decrease in proportion thereof to the total saccharide. In consideration of this result and the fact that the reaction time at which a large amount of trisaccharide FOS was present, a small amount of tetra- or higher-saccharide FOS was present, and the disaccharide was consumed efficiently is desirable from the viewpoint of industrial use, it was considered reasonable to evaluate the functions of the β-fructofuranosidases based on the amounts of FOSs produced at the point of time when the disaccharide was consumed up to 10 to 15%. Therefore, in the reviews on the improved β-fructofuranosidase in Example 2 et seq., the functions of the β-fructofuranosidases were evaluated based on the amounts of FOSs produced at the point of time when the disaccharide was consumed up to 10 to 15%.

TABLE 8

| Amounts (% (w/w)) of FOSs produced, relative to all saccharides, for wild-type β-fructofuranosidase | | | | |
|---|---|---|---|---|
| Reaction time (hr) | Monosaccharide (% (w/w)) | Disaccharide (% (w/w)) | Trisaccharide (% (w/w)) | Tetra- or higher-saccharide (% (w/w)) |
| 0 | 0 | 100 | 0 | 0 |
| 1 | 18.0 | 31.6 | 43.5 | 6.9 |
| 1.5 | 22.1 | 19.4 | 45.7 | 12.8 |
| 2 | 24.2 | 13.8 | 43.4 | 18.5 |
| 2.5 | 25.2 | 11.7 | 41.4 | 21.7 |
| 3 | 26.1 | 10.8 | 38.8 | 24.4 |
| 3.5 | 27.0 | 10.2 | 36.0 | 26.9 |
| 4 | 27.8 | 10.0 | 33.3 | 28.9 |
| 6 | 30.0 | 9.6 | 25.9 | 34.5 |
| 8 | 33.5 | 11.1 | 21.4 | 34.0 |

Example 2: Evaluation (1) of Improved Mutants of β-Fructofuranosidase

In Example 2, mutated β-fructofuranosidase-Gly81 (sometimes referred to as "AfBFFase-Gly81" herein) and mutated β-fructofuranosidase-Leu141 (sometimes referred to as "AfBFFase-Leu141" herein) in which glycine (Gly81) as the amino acid at the $81^{st}$ position and leucine (Leu141) as the amino acid at the $141^{st}$ position, respectively, from the amino terminal (N-terminal) of the amino acid sequence (SEQ ID NO: 1) of the wild-type β-fructofuranosidase of Example 1 were mutated were used to review the amounts of FOSs produced.

(1) Method a. Preparation of Plasmid of Improved β-Fructofuranosidase

Plasmids of AfBFFase-Gly81 and AfBFFase-Leu141 were prepared by the following procedures.

(i) PCR

Inverse PCR was performed using pHFT2_WT-AfBFFase prepared in Example 1 as a template. Tables 9 and 10 indicate primer base sequences for substituting the amino acid at the $81^{st}$ position and the amino acid at the $141^{st}$ position, respectively, with other amino acids. The PCR composition and PCR conditions were the same as those in Tables 4 and 5 of Example 1.

TABLE 9

| Primar base sequence (AfBFFase-Gly81) | | |
|---|---|---|
| Oligo DNA | | Base sequence |
| G81A_Inverse_Fw | (SEQ ID NO: 4) | GCTGACGGCATTGCC GGTGCAACTACCGCC |
| G81D_Inverse_Fw | (SEQ ID NO: 5) | GATGACGGCATTGCC GGTGCAACTACCGCC AACCTG |
| G81E_Inverse_Fw | (SEQ ID NO: 6) | GAGGACGGCATTGCC GGTGGAACTACCGCC AACCTG |
| G81F_Inverse_Fw | (SEQ ID NO: 7) | TTTGACGGCATTGCC GGTGCAACTACCGCC AACCTG |
| G81H_Inverse_Fw | (SEQ ID NO: 8) | CATGACGGCATTGCC GGTGCAACTACCGCC AACCTG |
| G81I_Inverse_Fw | (SEQ ID NO: 9) | ATTGACGGCATTGCC GGTGCAACTACCGCC AACCTG |
| G81K_Inverse_Fw | (SEQ ID NO: 10) | AAGGACGGCATTGCC GGTGCAACTACCGCC AACCTG |
| G81L_Inverse_Fw | (SEQ ID NO: 11) | CTTGACGGCATTGCC GGTGCAACTACCGCC AACCTG |
| G81M_Inverse_Fw | (SEQ ID NO: 12) | ATGGACGGCATTGCC GGTGCAACTACCGCC AACCTG |
| G81N_Inverse_Fw | (SEQ ID NO: 13) | AATGACGGCATTGCC GGTGCAACTACCGCC AACCTG |
| G81P_Inverse_Fw | (SEQ ID NO: 14) | CCTGACGGCATTGCC GGTGCAACTACCGCC AACCTG |
| G81Q_Inverse_Fw | (SEQ ID NO: 15) | CAGGACGGCATTGCC GGTGCAACTACCGCC AACCTG |
| G81R_Inverse_Fw | (SEQ ID NO: 16) | CGTGACGGCATTGCC GGTGCAACTACCGCC AACCTG |
| G81S_Inverse_Fw | (SEQ ID NO: 17) | TCTGACGGCATTGCC GGTGCAACTACCGCC |
| G81T_Inverse_Fw | (SEQ ID NO: 18) | ACTGACGGCATTGCC GGTGCAACTACCGCC AACCTG |

TABLE 9-continued

| Primar base sequence (AfBFFase-Gly81) | | |
|---|---|---|
| Oligo DNA | | Base sequence |
| G81V_Inverse_Fw | (SEQ ID NO: 19) | GTTGACGGCATTGCC GGTGCAACTACCGCC |
| G81W_Inverse_Fw | (SEQ ID NO: 20) | TGGGACGGCATTGCC GGTGCAACTACCGCC |
| G81Y_Inverse_Fw | (SEQ ID NO: 21) | TATGACGGCATTGCC GGTGCAACTACCGCC |
| G81X_Inverse_Rv | (SEQ ID NO: 22) | ATCATGCAGGAATCC AACGTGAAAAAGTCC |

Fw: Forward primer
Rv: Reverse primer

TABLE 10

| Primer base sequence (AfBFFase-Leu141) | | |
|---|---|---|
| Oligo DNA | | Base sequence |
| L141A_Inverse_Fw | (SEQ ID NO: 23) | GCGCCAATCCATTGG AGTATTCCCTATACG CGCGT |
| L141D_Inverse_Fw | (SEQ ID NO: 24) | GACCCAATCCATTGG AGTATTCCCTATACG CGCGGT |
| L141E_Inverse_Fw | (SEQ ID NO: 25) | GAGCCAATCCATTGG AGTATTCCCTATACG CGCGGT |
| L141F_Inverse_Fw | (SEQ ID NO: 26) | TTCCCAATCCATTGG AGTATTCCCTATACG CGCGGT |
| L141G_Inverse_Fw | (SEQ ID NO: 27) | GGGCCAATCCATTGG AGTATTCCCTATACG CGCGGT |
| L141H_Inverse_Fw | (SEQ ID NO: 28) | CACCCAATCCATTGG AGTATTCCCTATACG CGCGGT |
| L141I_Inverse_Fw | (SEQ ID NO: 29) | ATCCCAATCCATTGG AGTATTCCCTATACG CGCGGT |
| L141K_Inverse_Fw | (SEQ ID NO: 30) | AAGCCAATCCATTGG AGTATTCCCTATACG CGCGGT |
| L141M_Inverse_Fw | (SEQ ID NO: 31) | ATGCCAATCCATTGG AGTATTCCCTATACG CGCGGT |
| L141N_Inverse_Fw | (SEQ ID NO: 32) | AACCCAATCCATTGG AGTATTCCCTATACG CGCGGT |
| L141P_Inverse_Fw | (SEQ ID NO: 33) | CCGCCAATCCATTGG AGTATTCCCTATACG CGCGGT |
| L141Q_Inverse_Fw | (SEQ ID NO: 34) | CAGCCAATCCATTGG AGTATTCCCTATACG CGCGGT |
| L141R_Inverse_Fw | (SEQ ID NO: 35) | CGGCCAATCCATTGG AGTATTCCCTATACG CGCGGT |

TABLE 10-continued

| Primer base sequence (AfBFFase-Leu141) | | |
|---|---|---|
| Oligo DNA | | Base sequence |
| L141S_Inverse_Fw | (SEQ ID NO: 36) | TCGCCAATCCATTGG AGTATTCCCTATACG CGCGGT |
| L141T_Inverse_Fw | (SEQ ID NO: 37) | ACGCCAATCCATTGG AGTATTCCCTATACG CGCGGT |
| L141V_Inverse_Fw | (SEQ ID NO: 38) | GTGCCAATCCATTGG AGTATTCCCTATACG CGCGGT |
| L141W_Inverse_Fw | (SEQ ID NO: 39) | TGGCCAATCCATTGG AGTATTCCCTATACG CGCGGT |
| L141Y_Inverse_Fw | (SEQ ID NO: 40) | TACCCAATCCATTGG AGTATTCCCTATACG CGCGGT |
| L141X_Inverse_Rv | (SEQ ID NO: 41) | AAATGAGACAGATGT ATACAGCAACGTAGG GGTATT |

Fw: Forward primer
Rv: Reverse primer (ii) Restriction Enzyme Treatment

While the template DNA derived from *E. coli* is methylated, the DNA amplified by PCR is not methylated, and thus the template DNA can be decomposed and removed by DpnI (restriction enzyme). Therefore, 1 μL of DpnI was added to each amplified PCR product, and the product was subjected to restriction enzyme treatment under conditions of 37° C., 1 hour and still-standing. Then, gel extraction was performed in the same manner as described in Example 1, item (1), a (iii).

(iii) Phosphorylation

The 5' end of the DNA gel-extracted in (ii) above was phosphorylated. The composition of and conditions for phosphorylation are indicated in Tables 11 and 12, respectively. After the phosphorylation, the PCR product was eluted in an amount of L using FastGene Gel/PCR Extraction Kit (NIPPON Genetics Co., Ltd.).

TABLE 11

| Composition of phosphorylation | |
|---|---|
| Composition | Total amount 30 μL |
| Template DNA | 23.5 μL |
| 10 × T4 Polynucleotide Kinase Reaction Buffer | 3.0 μL |
| 10 mM ATP | 2.4 μL |
| 0.1M DTT | 0.5 μL |
| T4 Polynucleotide Kinase | 0.6 μL |

TABLE 12

| Phosphorylation reaction condition | |
|---|---|
| Temperature | Time |
| 37 °C | 2 hr |
| 75 °C | 15 min |
| 25 °C | 2 min |
| 8 °C | Retained |

(iv) Ligation

To 5 μL of an eluate of the PCR product, 5 μL (equal amount) of Ligation-Convenience Kit (NIPPON Genetics Co., Ltd.) was added, and the mixture was reacted at 16° C. for 15 minutes.

(v) Transformation of *E. coli* JM109

As described in Example 1, item (1) a (vi), *E. coli* JM109 was transformed using the ligation solution reacted in (iv) above, and it was confirmed, by DNA sequencing service, that a mutation had been introduced into the desired location of the plasmid (this plasmid is sometimes referred to as "pHFT2_AfBFFase-G81" herein).

b. Protein Expression and Purification (i) Transformation and Culture of *E. coli* BL21 (DE3)

*E. coli* BL21 (DE3) was transformed and cultured using pHFT2_AfBFFase-G81 in the same manner as described in Example 1, item (1) b (i).

(ii) Purification by Affinity Chromatography

Purification by affinity chromatography was performed in the same manner as described in Example 1, item (1) b (ii).

(iii) Purification by Gel Filtration Chromatography

Purification by gel filtration chromatography was performed in the same manner as described in Example 1, item (1) b (iii).

(iv) SDS-PAGE

In the same manner as described in Example 1, item (1) b (iv), SDS-PAGE was performed, and it was confirmed that the proteins of interest had been purified.

c. Evaluation of Amount of FOS Produced (i) Enzymatic Reaction

The enzymatic reaction was performed in the same manner as described in Example 1, item (1) c (i), except that the reaction times were changed to 0 hours, 1 hour, 2 hours, and 4 hours.

(ii) Liquid Chromatography (HPLC) Analysis

The amounts of FOSs produced were calculated by HPLC analysis in the same manner as described in Example 1, item (1) c (ii).

(2) Result

Figure 2:
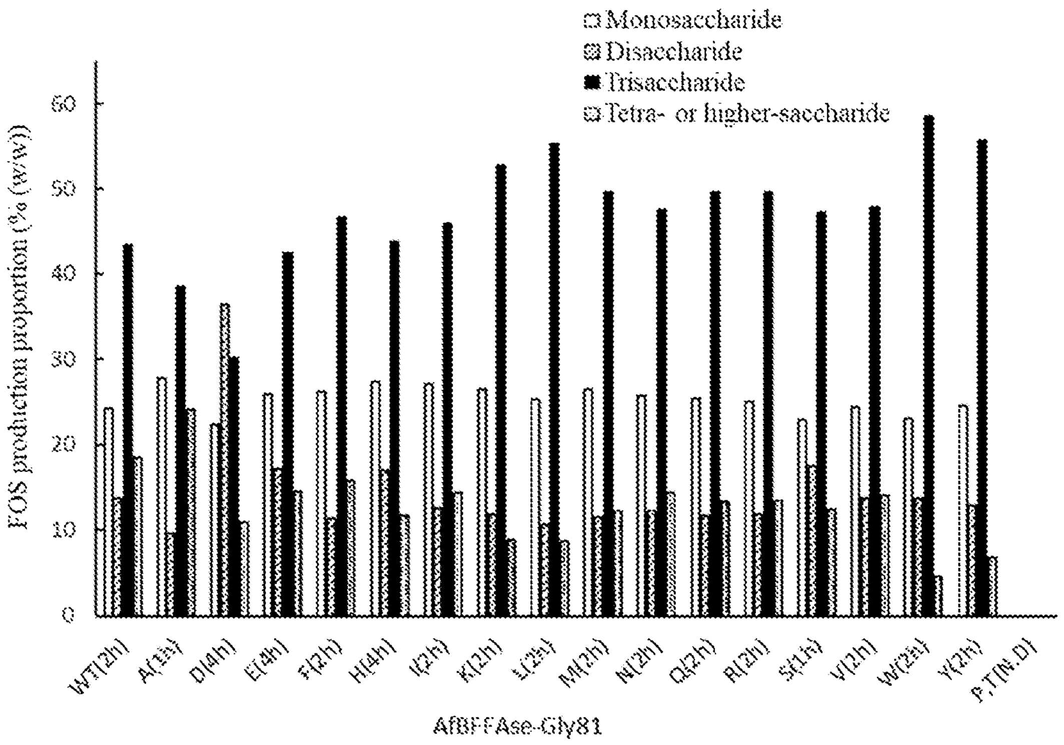
FIG. 2 shows the production proportions of FOSs (monosaccharide: glucose and fructose; disaccharide: sucrose; trisaccharide: trisaccharide FOS; and tetra- or higher-saccharide: tetra- or higher-saccharide FOS) by mutated β-fructofuranosidase-Gly81 (AfBFFase-Gly81) in which glycine (Gly81), which is an amino acid at the $81^{st}$ position from an amino terminal (N-terminal) of the amino acid sequence (SEQ ID NO: 1) of the wild-type β-fructofuranosidase (WT), is mutated. The alphabet letter on the horizontal axis indicates the amino acid with which Gly81 is substituted, and the numerical value in parentheses indicates the reaction time (hr).
Figure 3:
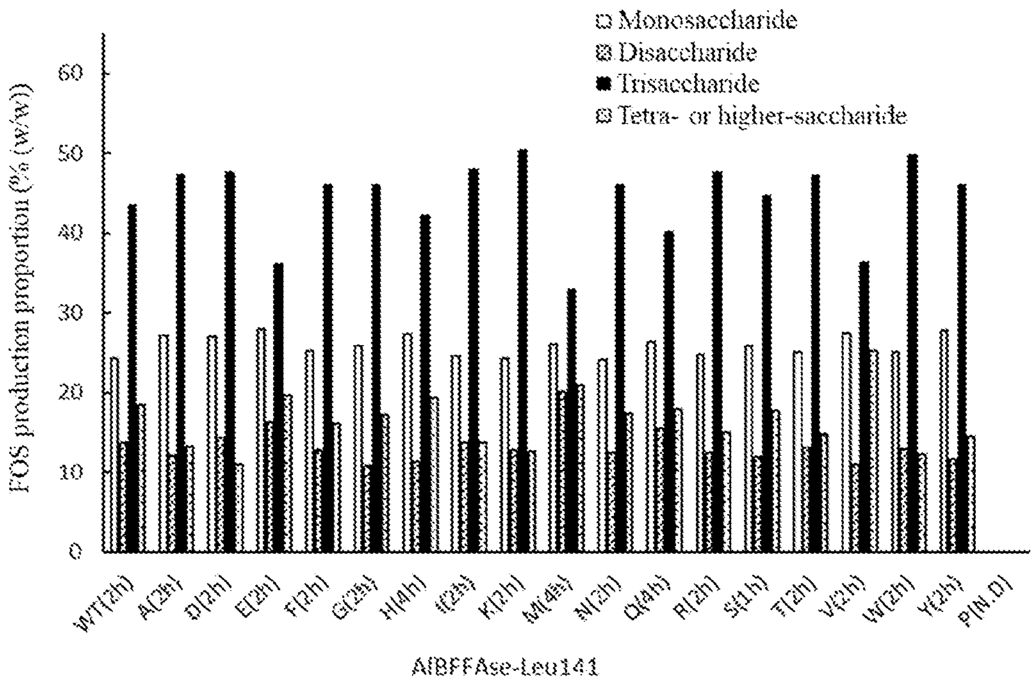
FIG. 3 shows the production proportions of FOSs (monosaccharide: glucose and fructose; disaccharide: sucrose; trisaccharide: trisaccharide FOS; and tetra- or higher-saccharide: tetra- or higher-saccharide FOS) by mutated β-fructofuranosidase-Leu141 (AfBFFase-Leu141) in which leucine (Leu141) at the $141^{st}$ position from the amino terminal (N-terminal) of the amino acid sequence (SEQ ID NO: 1) of the wild-type β-fructofuranosidase (WT) is mutated. The alphabet letter on the horizontal axis indicates the amino acid with which Leu141 is substituted, and the numerical value in parentheses indicates the reaction time (hr).

The results were as shown in Tables 13 and 14 and FIGS. 2 and 3.

For AfBFFase-Gly81, glycine (G) at the 81$^{st}$ position was substituted with 18 types of amino acids other than glycine (G) and cysteine (C) (alanine (A), aspartic acid (D), glutamic acid (E), phenylalanine (F), histidine (H), isoleucine (I), lysine (K), leucine (L), methionine (M), asparagine (N), glutamine (Q), arginine (R), serine (S), valine (V), tryptophan (W), tyrosine (Y), proline (P) and threonine (T)), and the amounts of FOSs produced were measured. Of the 18 types of mutants, the 15 types of mutants in which glycine (G) was substituted with the amino acids except alanine (A), proline (P), and threonine (T) were confirmed to have an increased production proportion of trisaccharide FOS or a decreased production proportion of tetra- or higher-saccharide. Among them, when glycine (G) was substituted with phenylalanine (F), histidine (H), isoleucine (I), lysine (K), leucine (L), and methionine (M), asparagine (N), glutamine (Q), arginine (R), serine (S), valine (V), tryptophan (W), or tyrosine (Y), AfBFFase-Gly81 was confirmed to have an increased production proportion of trisaccharide FOS relative to that of WT-AfBFFase. The production proportion of tetra- or higher-saccharide FOS was confirmed to be remarkably decreased when glycine (G) was substituted with aspartic acid (D) or glutamic acid (E). The production proportion of trisaccharide FOS was highest in the tryptophan (W) mutant (58.5%) and second highest in the tyrosine (Y) mutant (55.7%).

For AfBFFase-Leu141, leucine (L) at the 141$^{st}$ position was substituted with 18 types of amino acids other than leucine (L) and cysteine (C) (alanine (A), aspartic acid (D), glutamic acid (E), phenylalanine (F), glycine (G), histidine (H), isoleucine (I), lysine (K), methionine (M), asparagine (N), glutamine (Q), arginine (R), serine (S), threonine (T), valine (V), tryptophan (W), tyrosine (Y) and proline (P)), and the amounts of FOSs produced were measured. Of the 18 types of mutants, the 13 types of mutants in which leucine (L) was substituted with the amino acids except glutamic acid (E), histidine (H), methionine (M), valine (V) and proline (P) were confirmed to have an increased production proportion of trisaccharide FOS or a decreased production proportion of tetra- or higher-saccharide relative to that of WT-AfBFFase. In particular, the mutants in which leucine (L) was substituted with alanine (A), aspartic acid (D), isoleucine (I), lysine (K), arginine (R), threonine (T) or tryptophan (W) were confirmed to have a production proportion of trisaccharide FOS exceeding 47%. The production proportion of trisaccharide FOS was highest in the lysine (K) mutant (50.4%) and second highest in tryptophan (W) mutant (49.7%).

TABLE 13

Amounts (% (w/w)) of FOSs produced, relative to all saccharides, for AfBFFase-Gly81

| Gly81 mutant* (Reaction time**) | Monosaccharide (% (w/w)) | Disaccharide (% (w/w)) | Trisaccharide (% (w/w)) | Tetra- or higher-saccharide (% (w/w)) |
|---|---|---|---|---|
| WT (control) (2) | 24.3 | 13.8 | 43.4 | 18.5 |
| A (1) | 27.8 | 9.6 | 38.5 | 24.1 |
| D (4) | 22.3 | 36.5 | 30.2 | 11.0 |
| E (4) | 25.9 | 17.1 | 42.4 | 14.6 |
| F (2) | 26.2 | 11.3 | 46.7 | 15.8 |
| H (4) | 27.5 | 17.0 | 43.9 | 11.6 |
| I (2) | 27.1 | 12.7 | 45.9 | 14.3 |
| K (2) | 26.5 | 11.9 | 52.8 | 8.8 |
| L (2) | 25.3 | 10.7 | 55.3 | 8.7 |
| M (2) | 26.4 | 11.6 | 49.7 | 12.3 |
| N (2) | 25.8 | 12.2 | 47.6 | 14.4 |
| Q (2) | 25.4 | 11.6 | 49.7 | 13.3 |
| R (2) | 25.1 | 11.8 | 49.7 | 13.4 |
| S (1) | 22.9 | 17.4 | 47.2 | 12.5 |
| V (2) | 24.4 | 13.8 | 47.8 | 14.0 |
| W (2) | 23.1 | 13.8 | 58.5 | 4.6 |
| Y (2) | 24.6 | 12.9 | 55.7 | 6.8 |
| P, T (N.D) | | | | |

*The Gly81 mutant represents an amino acid mutant in which glycine at the 81$^{st}$ position from the N terminal of the amino acid sequence (SEQ ID NO: 1) of WO-AfBFFase is mutated.

**The reaction time is indicated in hour.

[Table 14]

TABLE 14

Amounts (% (w/w)) of FOSs produced, relative to all saccharides, for AfBFFase-Leu141

| Leu141 mutant* (Reaction time**) | Monosaccharide (% (w/w)) | Disaccharide (% (w/w)) | Trisaccharide (% (w/w)) | Tetra- or higher-saccharide (% (w/w)) |
|---|---|---|---|---|
| WT (control) (2) | 24.3 | 13.8 | 43.4 | 18.5 |
| A (2) | 27.2 | 12.1 | 47.4 | 13.3 |
| D (2) | 27.1 | 14.3 | 47.6 | 11.0 |
| E (2) | 28.0 | 16.3 | 36.1 | 19.6 |
| F (2) | 25.3 | 12.7 | 46.0 | 16.0 |
| G (2) | 26.0 | 10.8 | 46.0 | 17.2 |
| H (4) | 27.2 | 11.4 | 42.1 | 19.3 |

TABLE 14-continued

| Amounts (% (w/w)) of FOSs produced, relative to all saccharides, for AfBFFase-Leu141 | | | | |
|---|---|---|---|---|
| Leu141 mutant* (Reaction time**) | Mono-saccharide (% (w/w)) | Disaccharide (% (w/w)) | Trisaccharide (% (w/w)) | Tetra- or higher-saccharide (% (w/w)) |
| I (2) | 24.6 | 13.7 | 48.0 | 13.7 |
| K (2) | 24.3 | 12.7 | 50.4 | 12.6 |
| M (4) | 26.1 | 20.1 | 32.8 | 21.0 |
| N (2) | 24.1 | 12.4 | 46.1 | 17.4 |
| Q (4) | 26.4 | 15.6 | 40.1 | 17.9 |
| R (2) | 24.8 | 12.5 | 47.6 | 15.1 |
| S (1) | 25.9 | 11.9 | 44.5 | 17.7 |
| T (2) | 25.0 | 13.0 | 47.1 | 14.9 |
| V (2) | 27.5 | 11.0 | 36.3 | 25.2 |
| W (2) | 25.2 | 12.9 | 49.7 | 12.2 |
| Y (2) | 27.8 | 11.7 | 46.0 | 14.5 |
| P (N.D) | | | | |

*The Leu141 mutant represents an amino acid mutant in which leucine at the 141$^{st}$ position from the N terminal of the amino acid sequence (SEQ ID NO: 1) of WO-AfBFFase is mutated.
**The reaction time is indicated in hour.

Example 3: Evaluation (2) of Improved Mutants of β-Fructofuranosidase

In Example 3, a double-mutated improved β-fructofuranosidase (sometimes referred to as "AfBFFase-Gly81-Leu141" herein) in which both of glycine (Gly81) at the 81$^{st}$ position and leucine (Leu141) at the 141$^{st}$ position from the N-terminal of the amino acid sequence (SEQ ID NO: 1) of WT-AfBFFase were mutated was used to review the amounts of FOSs produced.

(1) Method a. Preparation of Plasmid of Improved β-Fructofuranosidase (Double-Mutated)

Inverse PCR was performed using the plasmids pHFT2_AfBFFase-G81Y and pHFT2_AfBFFase-G81W as templates and the primers for Leu141Y and Leu141W to prepare four plasmids pHFT2_AfBFFase-G81Y-L141Y, pHFT2_AfBFFase-G81Y-L141W, pHFT2_AfBFFase-G81W-Leu141Y and pHFT2_AfBFFase-G81W-L141W. The same PCR composition and conditions, restriction enzyme treatment, phosphorylation, and transformation of *E. coli* JM109 as those described in Example 2, item (1) a were adopted.

b. Protein Expression and Purification

Transformation and culture of *E. coli* BL21 (DE3), purification by affinity chromatography, and purification by gel filtration chromatography were performed in the same manners as described in Example 2, item (1) b.

c. Evaluation of Amount of FOS Produced

The enzymatic reaction and HPLC analysis were performed in the same manners as described in Example 2, item (1) c.

(2) Result

Figure 4:
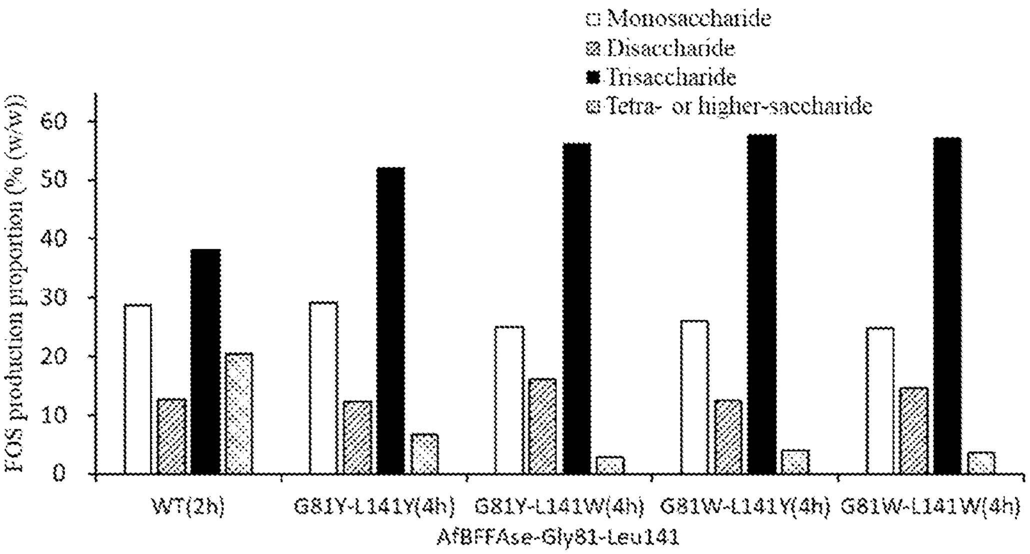
FIG. 4 shows the production proportions of FOSs (monosaccharide: glucose and fructose; disaccharide: sucrose; trisaccharide: trisaccharide FOS; and tetra- or higher-saccharide: tetra- or higher-saccharide FOS) by a double-mutated improved β-fructofuranosidase (AfBFFase-Gly81-Leu141) in which both of glycine (Gly81) at the $81^{st}$ position and leucine (Leu141) at the $141^{st}$ position, from the amino terminal (N-terminal) of the amino acid sequence (SEQ ID NO: 1) of the wild-type β-fructofuranosidase (WT), are mutated. Of the two alphabet letters on the horizontal axis, the left one indicates the amino acid with which Gly81 is substituted, the right one indicates the amino acid with which Leu141 are substituted, and the numerical values in parentheses indicate the reaction times (hr).

The results were as shown in Table 15 and FIG. 4.

AfBFFase-Gly81-Leu141 in which glycine (G) at the 81$^{st}$ position and leucine (L) at the 141$^{st}$ position were substituted with tyrosine (Y) and tryptophan (W), respectively, was confirmed to require a long time for consuming the disaccharide, but have a high production proportion of trisaccharide FOS and a low production proportion of tetra- or higher-saccharide FOS, as compared with those of WT-AfBFFase.

TABLE 15

| Amounts (% (w/w)) of FOSs produced, relative to all saccharides, for AfBFFase-Gly81-Leu141 | | | | |
|---|---|---|---|---|
| Gly81-Leu141 mutant* (Reaction time**) | Mono-saccharide (% (w/w)) | Disaccharide (% (w/w)) | Trisaccharide (% (w/w)) | Tetra- or higher-saccharide (% (w/w)) |
| WT (control) (2) | 28.6 | 12.7 | 38.2 | 20.5 |
| G81Y141Y (4 h) | 29.0 | 12.2 | 52.1 | 6.7 |
| G81Y141W (4 h) | 24.9 | 16.1 | 56.2 | 2.8 |
| G81W141Y (4 h) | 25.9 | 12.6 | 57.6 | 3.9 |
| G81W141W (4 h) | 24.7 | 14.7 | 57.0 | 3.6 |

*The Gly81-Leu141 mutant represents an amino acid mutant in which glycine at the 81$^{st}$ position and leucine at the 141$^{st}$ position are mutated.
**The reaction time is indicated in hour.

The invention claimed is:

1. An β-fructofuranosidase consisting of an amino acid sequence of a β-fructofuranosidase in which either or both of an amino acid corresponding to the $81^{st}$ position from an amino terminal of an amino acid sequence shown in SEQ ID NO: 1 and an amino acid corresponding to the $141^{st}$ position from the amino terminal of the amino acid sequence shown in SEQ ID NO: 1 is/are substituted with another amino acid/other amino acids, wherein the amino acid corresponding to the $81^{st}$ position from the amino terminal is substituted with an amino acid selected from the group consisting of phenylalanine (F), histidine (H), isoleucine (I), lysine (K), leucine (L), methionine (M), asparagine (N), glutamine (Q), arginine (R), serine (S), valine (V), tryptophan (W) and tyrosine (Y), wherein the amino acid corresponding to the $141^{st}$ position from the amino terminal is substituted with an amino acid selected from the group consisting of alanine (A), aspartic acid (D), phenylalanine (F), glycine (G), lysine (K), asparagine (N), arginine (R), serine (S), threonine (T), tryptophan (W) and tyrosine (Y), and wherein the β-fructofuranosidase consists of an amino acid sequence having a sequence identity of 80% or more with the amino acid sequence of wild-type β-fructofuranosidase shown in SEQ ID NO: 1, and also having β-fructofuranosidase activity.

2. The β-fructofuranosidase according to claim 1, wherein the amino acid corresponding to the $81^{st}$ position from the amino terminal is substituted with an amino acid selected from the group consisting of lysine (K), leucine (L), tryptophan (W) and tyrosine (Y).

3. The β-fructofuranosidase according to claim 1, wherein the amino acid corresponding to the $141^{st}$ position from the amino terminal is substituted with an amino acid selected from the group consisting of alanine (A), aspartic acid (D), isoleucine (I), lysine (K), arginine (R), threonine (T), and tryptophan (W).

4. A polypeptide comprising an enzymatically active portion of the amino acid sequence of the β-fructofuranosidase according to claim 1, and having β-fructofuranosidase activity.

5. A polynucleotide encoding the β-fructofuranosidase according to claim 1.

6. An expression vector comprising the polynucleotide according to claim 5.

7. A transformant obtained by introducing the polynucleotide according to claim 5 into a host.

8. The transformant according to claim 7, wherein the host is selected from the group consisting of bacteria, yeasts, molds and filamentous fungi.

9. A method for manufacturing an β-fructofuranosidase, comprising the step of obtaining an β-fructofuranosidase from a culture of the transformant according to claim 7.

10. A method for manufacturing a fructooligosaccharide, comprising the step of bringing the β-fructofuranosidase according to claim 1 into contact with sucrose.

11. A method for manufacturing a 1-kestose crystal, comprising the steps of: manufacturing a fructooligosaccharide by carrying out the manufacture method according to claim 10; and crystallizing the fructooligosaccharide.

12. The β-fructofuranosidase according to claim 1, wherein the amino acid corresponding to the $81^{st}$ position from the amino terminal is substituted with an amino acid selected from the group consisting of phenylalanine (F), histidine (H), isoleucine (I), lysine (K), leucine (L), methionine (M), asparagine (N), glutamine (Q), arginine (R), serine(S), valine (V), tryptophan (W) and tyrosine (Y), and wherein the amino acid corresponding to the 141st position from the amino terminal is substituted with an amino acid selected from the group consisting of alanine (A), aspartic acid (D), phenylalanine (F), glycine (G), lysine (K), asparagine (N), arginine (R), serine(S), threonine (T), tryptophan (W) and tyrosine (Y).

13. The β-fructofuranosidase according to claim 1, wherein the amino acid corresponding to the 81st position from the amino terminal is substituted with tryptophan (W) or tyrosine (Y).

14. The β-fructofuranosidase according to claim 1, wherein the amino acid corresponding to the 141st position from the amino terminal is substituted with from lysine (K) or tryptophan (W).

15. The β-fructofuranosidase according to claim 12, wherein the amino acid corresponding to the 81st position from the amino terminal is substituted with tyrosine (Y) or tryptophan (W), and wherein the amino acid corresponding to the 141st position from the amino terminal is substituted with tyrosine (Y) or tryptophan (W).

* * * * *

SEQUENCE LISTING

```
Sequence total quantity: 41
SEQ ID NO: 1          moltype = AA  length = 654
FEATURE               Location/Qualifiers
source                1..654
                      mol_type = protein
                      organism = Aspergillus fijiensis
SEQUENCE: 1
MKLTTTTLAL ATGAAAAEAS YHLDTTAPPP TNLSTLPNNT LFHVWRPRAH ILPAEGQIGD  60
PCAHYTDPST GLFHVGFLHD GDGIAGATTA NLATYTDTSD NGSFLIQPGG KNDPVAVFDG  120
AVIPVGVNNT PTLLYTSVSF LPIHWSIPYT RGSETQSLAV ARDGGRRFDK LDQGPVIADH  180
PFAVDVTAFR DPFVFRSAKL DVLLSLDEEV ARNETAVQQA VDGWTEKNAP WYVAVSGGVH  240
GVGPAQFLYR QNGGNASEFQ YWEYLGEWWQ EATNSSWGDE GTWAGRWGFN FETGNVLFLT  300
EEGHDPQTGE VFVTLGTEGS GLPIVPQVSS IHDMLWAAGE VGVGSEQEGA KVEFSPSMAG  360
FLDWGFSAYA AAGKVLPASS AVSKTSGVEV DRYVSFVWLT GDQYEQADGF PTAQQGWTGS  420
LLLPRELKVQ TVENVVDNEL VREEGVSWVV GESDNQTARL RTLGITIARE TKAALLANGS  480
VTAEEDRTLQ TAAVVPFAQS PSSKFFVLTA QLEFPASARS SPLQSGFEIL ASELERTAIY  540
YQFSNESLVV DRSQTSAAAP TNPGLDSFTE SGKLRLFDVI ENGQEQVETL DLTVVVDNAV  600
VEVYANGRFA LSTWARSWYD NSTQIRFFHN GEGEVQFRNV SVSEGLYNAW PERN        654

SEQ ID NO: 2          moltype = DNA  length = 42
FEATURE               Location/Qualifiers
source                1..42
                      mol_type = other DNA
                      organism = synthetic construct
SEQUENCE: 2
attataggat cctcctacca tttggatacg actgcaccac cg                     42
```

```
SEQ ID NO: 3            moltype = DNA  length = 45
FEATURE                 Location/Qualifiers
source                  1..45
                        mol_type = other DNA
                        organism = synthetic construct
SEQUENCE: 3
attatactcg agttatcagt tgcgctcagg ccacgcgtta tataa                45

SEQ ID NO: 4            moltype = DNA  length = 30
FEATURE                 Location/Qualifiers
source                  1..30
                        mol_type = other DNA
                        organism = synthetic construct
SEQUENCE: 4
gctgacggca ttgccggtgc aactaccgcc                                 30

SEQ ID NO: 5            moltype = DNA  length = 36
FEATURE                 Location/Qualifiers
source                  1..36
                        mol_type = other DNA
                        organism = synthetic construct
SEQUENCE: 5
gatgacggca ttgccggtgc aactaccgcc aacctg                          36

SEQ ID NO: 6            moltype = DNA  length = 36
FEATURE                 Location/Qualifiers
source                  1..36
                        mol_type = other DNA
                        organism = synthetic construct
SEQUENCE: 6
gaggacggca ttgccggtgc aactaccgcc aacctg                          36

SEQ ID NO: 7            moltype = DNA  length = 36
FEATURE                 Location/Qualifiers
source                  1..36
                        mol_type = other DNA
                        organism = synthetic construct
SEQUENCE: 7
tttgacggca ttgccggtgc aactaccgcc aacctg                          36

SEQ ID NO: 8            moltype = DNA  length = 36
FEATURE                 Location/Qualifiers
source                  1..36
                        mol_type = other DNA
                        organism = synthetic construct
SEQUENCE: 8
catgacggca ttgccggtgc aactaccgcc aacctg                          36

SEQ ID NO: 9            moltype = DNA  length = 36
FEATURE                 Location/Qualifiers
source                  1..36
                        mol_type = other DNA
                        organism = synthetic construct
SEQUENCE: 9
attgacggca ttgccggtgc aactaccgcc aacctg                          36

SEQ ID NO: 10           moltype = DNA  length = 36
FEATURE                 Location/Qualifiers
source                  1..36
                        mol_type = other DNA
                        organism = synthetic construct
SEQUENCE: 10
aaggacggca ttgccggtgc aactaccgcc aacctg                          36

SEQ ID NO: 11           moltype = DNA  length = 36
FEATURE                 Location/Qualifiers
source                  1..36
                        mol_type = other DNA
                        organism = synthetic construct
SEQUENCE: 11
cttgacggca ttgccggtgc aactaccgcc aacctg                          36

SEQ ID NO: 12           moltype = DNA  length = 36
FEATURE                 Location/Qualifiers
source                  1..36
                        mol_type = other DNA
                        organism = synthetic construct
SEQUENCE: 12
```

```
atggacggca ttgccggtgc aactaccgcc aacctg                        36

SEQ ID NO: 13          moltype = DNA  length = 36
FEATURE                Location/Qualifiers
source                 1..36
                       mol_type = other DNA
                       organism = synthetic construct
SEQUENCE: 13
aatgacggca ttgccggtgc aactaccgcc aacctg                        36

SEQ ID NO: 14          moltype = DNA  length = 36
FEATURE                Location/Qualifiers
source                 1..36
                       mol_type = other DNA
                       organism = synthetic construct
SEQUENCE: 14
cctgacggca ttgccggtgc aactaccgcc aacctg                        36

SEQ ID NO: 15          moltype = DNA  length = 36
FEATURE                Location/Qualifiers
source                 1..36
                       mol_type = other DNA
                       organism = synthetic construct
SEQUENCE: 15
caggacggca ttgccggtgc aactaccgcc aacctg                        36

SEQ ID NO: 16          moltype = DNA  length = 36
FEATURE                Location/Qualifiers
source                 1..36
                       mol_type = other DNA
                       organism = synthetic construct
SEQUENCE: 16
cgtgacggca ttgccggtgc aactaccgcc aacctg                        36

SEQ ID NO: 17          moltype = DNA  length = 30
FEATURE                Location/Qualifiers
source                 1..30
                       mol_type = other DNA
                       organism = synthetic construct
SEQUENCE: 17
tctgacggca ttgccggtgc aactaccgcc                               30

SEQ ID NO: 18          moltype = DNA  length = 36
FEATURE                Location/Qualifiers
source                 1..36
                       mol_type = other DNA
                       organism = synthetic construct
SEQUENCE: 18
actgacggca ttgccggtgc aactaccgcc aacctg                        36

SEQ ID NO: 19          moltype = DNA  length = 30
FEATURE                Location/Qualifiers
source                 1..30
                       mol_type = other DNA
                       organism = synthetic construct
SEQUENCE: 19
gttgacggca ttgccggtgc aactaccgcc                               30

SEQ ID NO: 20          moltype = DNA  length = 30
FEATURE                Location/Qualifiers
source                 1..30
                       mol_type = other DNA
                       organism = synthetic construct
SEQUENCE: 20
tgggacggca ttgccggtgc aactaccgcc                               30

SEQ ID NO: 21          moltype = DNA  length = 30
FEATURE                Location/Qualifiers
source                 1..30
                       mol_type = other DNA
                       organism = synthetic construct
SEQUENCE: 21
tatgacggca ttgccggtgc aactaccgcc                               30

SEQ ID NO: 22          moltype = DNA  length = 30
FEATURE                Location/Qualifiers
source                 1..30
                       mol_type = other DNA
                       organism = synthetic construct
```

```
SEQUENCE: 22
atcatgcagg aatccaacgt gaaaaagtcc                                     30

SEQ ID NO: 23           moltype = DNA  length = 36
FEATURE                 Location/Qualifiers
source                  1..36
                        mol_type = other DNA
                        organism = synthetic construct
SEQUENCE: 23
gcgccaatcc attggagtat tccctatacg cgcggt                              36

SEQ ID NO: 24           moltype = DNA  length = 36
FEATURE                 Location/Qualifiers
source                  1..36
                        mol_type = other DNA
                        organism = synthetic construct
SEQUENCE: 24
gacccaatcc attggagtat tccctatacg cgcggt                              36

SEQ ID NO: 25           moltype = DNA  length = 36
FEATURE                 Location/Qualifiers
source                  1..36
                        mol_type = other DNA
                        organism = synthetic construct
SEQUENCE: 25
gagccaatcc attggagtat tccctatacg cgcggt                              36

SEQ ID NO: 26           moltype = DNA  length = 36
FEATURE                 Location/Qualifiers
source                  1..36
                        mol_type = other DNA
                        organism = synthetic construct
SEQUENCE: 26
ttcccaatcc attggagtat tccctatacg cgcggt                              36

SEQ ID NO: 27           moltype = DNA  length = 36
FEATURE                 Location/Qualifiers
source                  1..36
                        mol_type = other DNA
                        organism = synthetic construct
SEQUENCE: 27
gggccaatcc attggagtat tccctatacg cgcggt                              36

SEQ ID NO: 28           moltype = DNA  length = 36
FEATURE                 Location/Qualifiers
source                  1..36
                        mol_type = other DNA
                        organism = synthetic construct
SEQUENCE: 28
cacccaatcc attggagtat tccctatacg cgcggt                              36

SEQ ID NO: 29           moltype = DNA  length = 36
FEATURE                 Location/Qualifiers
source                  1..36
                        mol_type = other DNA
                        organism = synthetic construct
SEQUENCE: 29
atcccaatcc attggagtat tccctatacg cgcggt                              36

SEQ ID NO: 30           moltype = DNA  length = 36
FEATURE                 Location/Qualifiers
source                  1..36
                        mol_type = other DNA
                        organism = synthetic construct
SEQUENCE: 30
aagccaatcc attggagtat tccctatacg cgcggt                              36

SEQ ID NO: 31           moltype = DNA  length = 36
FEATURE                 Location/Qualifiers
source                  1..36
                        mol_type = other DNA
                        organism = synthetic construct
SEQUENCE: 31
atgccaatcc attggagtat tccctatacg cgcggt                              36

SEQ ID NO: 32           moltype = DNA  length = 36
FEATURE                 Location/Qualifiers
source                  1..36
                        mol_type = other DNA
```

```
                      organism = synthetic construct
SEQUENCE: 32
aacccaatcc attggagtat tccctatacg cgcggt                            36

SEQ ID NO: 33         moltype = DNA  length = 36
FEATURE               Location/Qualifiers
source                1..36
                      mol_type = other DNA
                      organism = synthetic construct
SEQUENCE: 33
ccgccaatcc attggagtat tccctatacg cgcggt                            36

SEQ ID NO: 34         moltype = DNA  length = 36
FEATURE               Location/Qualifiers
source                1..36
                      mol_type = other DNA
                      organism = synthetic construct
SEQUENCE: 34
cagccaatcc attggagtat tccctatacg cgcggt                            36

SEQ ID NO: 35         moltype = DNA  length = 36
FEATURE               Location/Qualifiers
source                1..36
                      mol_type = other DNA
                      organism = synthetic construct
SEQUENCE: 35
cggccaatcc attggagtat tccctatacg cgcggt                            36

SEQ ID NO: 36         moltype = DNA  length = 36
FEATURE               Location/Qualifiers
source                1..36
                      mol_type = other DNA
                      organism = synthetic construct
SEQUENCE: 36
tcgccaatcc attggagtat tccctatacg cgcggt                            36

SEQ ID NO: 37         moltype = DNA  length = 36
FEATURE               Location/Qualifiers
source                1..36
                      mol_type = other DNA
                      organism = synthetic construct
SEQUENCE: 37
acgccaatcc attggagtat tccctatacg cgcggt                            36

SEQ ID NO: 38         moltype = DNA  length = 36
FEATURE               Location/Qualifiers
source                1..36
                      mol_type = other DNA
                      organism = synthetic construct
SEQUENCE: 38
gtgccaatcc attggagtat tccctatacg cgcggt                            36

SEQ ID NO: 39         moltype = DNA  length = 36
FEATURE               Location/Qualifiers
source                1..36
                      mol_type = other DNA
                      organism = synthetic construct
SEQUENCE: 39
tggccaatcc attggagtat tccctatacg cgcggt                            36

SEQ ID NO: 40         moltype = DNA  length = 36
FEATURE               Location/Qualifiers
source                1..36
                      mol_type = other DNA
                      organism = synthetic construct
SEQUENCE: 40
tacccaatcc attggagtat tccctatacg cgcggt                            36

SEQ ID NO: 41         moltype = DNA  length = 36
FEATURE               Location/Qualifiers
source                1..36
                      mol_type = other DNA
                      organism = synthetic construct
SEQUENCE: 41
aaatgagaca gatgtataca gcaacgtagg ggtatt                            36
```